(12) United States Patent
Parent et al.

(10) Patent No.: US 9,139,814 B2
(45) Date of Patent: Sep. 22, 2015

(54) CULTURE MEDIUM FOR MYOBLASTS, PRECURSORS THEREOF AND DERIVATIVES THEREOF

(75) Inventors: Victor-Alain Parent, Quebec (CA); Alain Garnier, Quebec (CA); Jacques P. Tremblay, Quebec (CA)

(73) Assignee: Universite Laval, Quebec (CA)

(*) Notice: Subject to any disclaimer, the term of this patent is extended or adjusted under 35 U.S.C. 154(b) by 280 days.

(21) Appl. No.: 13/120,141

(22) PCT Filed: Sep. 22, 2009

(86) PCT No.: PCT/CA2009/001342
§ 371 (c)(1),
(2), (4) Date: Jun. 23, 2011

(87) PCT Pub. No.: WO2010/031190
PCT Pub. Date: Mar. 25, 2010

(65) Prior Publication Data
US 2011/0250691 A1    Oct. 13, 2011

Related U.S. Application Data

(60) Provisional application No. 61/098,964, filed on Sep. 22, 2008.

(51) Int. Cl.
*C12N 5/02* (2006.01)
*C12N 5/077* (2010.01)
*A61K 35/12* (2015.01)

(52) U.S. Cl.
CPC .............. *C12N 5/0658* (2013.01); *A61K 35/12* (2013.01); *C12N 2500/25* (2013.01); *C12N 2500/84* (2013.01); *C12N 2500/99* (2013.01); *C12N 2501/105* (2013.01); *C12N 2501/11* (2013.01); *C12N 2501/115* (2013.01); *C12N 2501/135* (2013.01)

(58) Field of Classification Search
CPC combination set(s) only.
See application file for complete search history.

(56) References Cited

U.S. PATENT DOCUMENTS

| 5,143,842 A | 9/1992 | Ham et al. | 435/240.2 |
| 5,435,999 A * | 7/1995 | Austin | 424/93.1 |
| 2006/0057124 A1 | 3/2006 | Shim et al. | 424/93.7 |

FOREIGN PATENT DOCUMENTS

WO    WO 90/15863 A1    12/1990

OTHER PUBLICATIONS

Austin et al., "Effects of leukaemia inhibitory factor and other cytokines on murine and human myoblast proliferation," *Journal of the Neurological Sciences* 112:185-191, 1992.
Brewer et al., "Optimized Survival of Hippocampal Neurons in B27-Supplemental Neurobasal™, a New Serum-free Medium Combination," *Journal of Neuroscience Research* 35:567-576, 1993.
Broussard et al., "IL-1β Impairs Insulin-Like Growth Factor I-Induced Differentiation and Downstream Activation Signals of the Insulin-Like Growth Factor I Receptor in Myoblasts," *The Journal of Immunology* 172:7713-7720, 2004.
Cantini et al., "Human Satellite Cell Proliferation In Vitro Is Regulated by Autocrine Secretion of IL-6 Stimulated by a Soluble Factor(s) Released by Activated Monocytes," *Biochemical and Biophysical Research Communications* 216(1):49-53, 1995.
Cantini et al., "Macrophage-secreted myogenic factors: a promising tool for greatly enhancing the proliferative capacity of myoblasts in vitro and in vivo," *Neurol. Sci.* 23:189-194, 2002.
Chakravarthy et al., "IGF-I restores satellite cell proliferative potential in immobilized old skeletal muscle," *J. Appl. Physiol.* 89:1365-1379, 2000.
Chargé et al., "Cellular and Molecular Regulation of Muscle Regeneration," *Physiol. Rev.* 84:209-238, 2004.
Chazaud et al., "Satellite cells attract monocytes and use macrophages as a support to escape apoptosis and enhance muscle growth," *The Journal of Cell Biology* 163(5):1133-1143, 2003.
Chevrel et al., "Contribution of tumour necrosis factor α and interleukin (IL) 1β to IL6 production, NF-κB nuclear translocation, and class I MHC expression in muscle cells: in vitro regulation with specific cytokine inhibitors," *Ann. Rheum. Dis.* 64:1257-1262, 2005.
Das et al., "A defined system to allow skeletal muscle differentiation and subsequent integration with silicon microstructures," *Biomaterials* 27:4374-4380, 2006.
Floss et al., "A role for FGF-6 in skeletal muscle regeneration," *Genes & Development* 11:2040-2051, 1997.
Girgenrath et al., "TWEAK, via its receptor Fn14, is a novel regulator of mesenchymal progenitor cells and skeletal muscle regeneration," *The EMBO Journal* 25:5826-5839, 2006.
Goto et al., "Serum-Free Culture Conditions for Analysis of Secretory Proteinases during Myogenic Differentiation of Mouse C2C12 Myoblasts," *Analytical Biochemistry* 272:135-142, 1999.
Ham et al., "Improved Media for Normal Human Muscle Satellite Cells: Serum-Free Clonal Growth and Enhanced Growth With Low Serum," *In Vitro Cellular & Developmental Biology* 24(8):833-844, 1988.
International Search Report for International Application No. PCT/CA2009/001342, mailed Dec. 22, 2009, 6 pages.
Kurek et al., "Leukaemia Inhibitory Factor and Other Cytokines as Factors Influencing Regeneration of Skeletal Muscle," *Basic Appl. Myol.* 8(5):347-360, 1998.
Lecoeur et al., "Intraurethral Transfer of Satellite Cells by Myofiber Implants Results in the Formation of Innervated Myotubes Exerting Tonic Contractions," *The Journal of Urology* 178:332-337, 2007.
Li, "TNF-α is a mitogen in skeletal muscle," *Am. J. Physiol. Cell Physiol.* 285:C370-C376, 2003.
Massimino et al., "ED2+ Macrophages Increase Selectively Myoblast Proliferation in Muscle Cultures," *Biochemical and Biophysical Research Communications* 235:754-759, 1997.

(Continued)

*Primary Examiner* — Allison Fox
*Assistant Examiner* — Yvonne Pyla
(74) *Attorney, Agent, or Firm* — Seed IP Law Group PLLC

(57) ABSTRACT

This application relates to a serum-free culture medium that enables the proliferation of cell of the myogenic lineage while maintaining their ability to differentiate into functional muscle cells. Also contemplated herewith are method of culturing cells of the myogenic lineages and uses of the cultured cells for the treatment or the alleviation of symptoms of a muscular deficiencies.

22 Claims, 11 Drawing Sheets

(56) References Cited

OTHER PUBLICATIONS

Miller et al., "Hepatocyte growth factor affects satellite cell activation and differentiation in regenerating skeletal muscle," *Am. J. Physiol. Cell Physiol.* 278:C174-C181, 2000.

Mizel, "The interleukins," *FASEB J.* 3:2379-2388, 1989.

Skuk et al., "Dystrophin Expression in Muscles of Duchenne Muscular Dystrophy Patients After High-Density Injections of Normal Myogenic Cells," *J. Neuropathol. Exp. Neurol.* 65(4):371-386, 2006.

White et al., "Leukaemia inhibitory factor increases myoblast replication and survival and affects extracellular matrix production: combined in vivo and in vitro studies in post-natal skeletal muscle," *Cell Tissue Res.* 306:129-141, 2001.

Zimmerman et al., "Formulation of a defined medium to maintain cell health and viability in vitro," *Methods in Cell Science* 22:43-49, 2000.

\* cited by examiner

CULTURE MEDIUM FOR MYOBLASTS, PRECURSORS THEREOF AND DERIVATIVES THEREOF

CROSS-REFERENCE TO RELATED APPLICATIONS

This is application claims priority from U.S. provisional application Ser. No. 61/098,964 filed on Sep. 22, 2008 and incorporated herewith by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 920116_401USPC_SEQUENCE_LISTING.txt. The text file is 36 KB, was created on Mar. 21, 2011, and is being submitted electronically via EFS-Web.

BACKGROUND OF THE INVENTION

Duchenne muscular dystrophy (DMD), with a prevalence of 1 boy out of 3500, is the most widely spread genetic disease (Voisin, 2004). This disease is characterized by the progressive weakening of muscles, resulting in muscular necrosis and fibrosis (Emery, 2003). An essential protein for muscle fibers stability, dystrophin, is missing or defective in muscle fibers of DMD patients. Dystrophin is a 427-kDa protein which connects the actin cytoskeleton to the cellular membrane (Bogdanovich et al. 2004). The function of this protein is to maintain the stability of the cellular membrane in order to support the stresses induced during muscular contractions (Carpenter et al. 1990). The absence of dystrophin increases the vulnerability of muscle fibers during their contraction. Consequently, constant muscular repair will be necessary, which will result in the premature senescence of myoblasts.

Cellular therapy, a therapy under development to counter DMD, has shown significant therapeutic effect in several studies in mice (Chen, Li et al. 1992) and humans (Gussoni et al. 1992; Huard et al. 1992; Huard et al. 1994; Skuk et al. 2006; Skuk et al. 2007). This curative approach is regarded as a promising treatment (Skuk and Tremblay, 2000). Presently, cellular therapy consists in injecting human myoblasts in the muscles of the DMD patients. The healthy myoblasts fuse to muscle fibers of the patients and partially restore the expression of dystrophin. This expression increases the strength of the treated muscle and restores at least partially their functionality, hence improving significantly the patient's quality of life. Nevertheless, some difficulties remain to be surmounted, of which the immunizing response against the injected myoblasts, the absence of fusion of myoblasts with undamaged fibers as well as the poor migration of the myoblasts in the muscle tissue. Moreover, the culture medium presently used for myoblast expansion contains blood serum and the production processes presently used are not adequate for the production of the large number of myoblasts that would be required to treat the whole muscle mass of a patient. Constant and rapid progresses are made on these fronts, through better understanding of myoblast and myogenic cell biology, transplantation and migration, the development of protocols to alleviate immuno-rejection, and the identification of alternative cell sources, e.g. pluripotent stem cells (Skuk et al. 2002). Cellular therapy therefore seems to be on the verge of being the very first accepted therapy against DMD.

In addition to the treatment of DMD, myoblast injections are also used for the treatment of myocardial infarction and for urethral sphincter insufficiency. Indeed, the grafts of myoblasts significantly improve the contractility as well as the viability of cardiac tissues and allows 41% restoration of the normal sphincter contractility (Yiou et al. 2004; Kahn, 2006).

The nutritional needs of in vitro cultured cells comprise a vast range of molecules, of which several are found in a basal medium, which contains the essential components necessary to the cellular metabolism and osmotic balance maintenance: salts, amino-acids, vitamins, sugars, lipids, trace elements, antioxidants and pH buffer (Ham and McKeehan 1979; Butler, 1991; Mather and Barnes 1998; Davis, 2002; Naomoto et al. 2005). The basal medium must be selected considering its compatibility with the type of cells to be cultured, as well as its performance with regards to predetermined responses of interest. The role of the basal medium can therefore either be to support proliferation, differentiation or quiescence of a given cell population (Zimmerman et al. 2000). Basal media known to support myoblast expansion are DMEM, F12, RPMI1640 (Goto et al. 1999) and MCDB120 (Ham et al. 1988).

The medium generally used to culture myoblasts in vitro (standard medium, STD) is MCDB120 supplemented with 15% fetal bovine serum (FBS), 10 ng/ml basic fibroblast growth factor (bFGF), 0.39 µg/ml dexamethasone and 0.5 mg/ml bovine serum albumin (BSA). Serum is an additive which allows the non-specific proliferation of a vast range of cell types. It is prepared from plasma, the liquid fraction of blood, from which clotting factors were removed. The principal sources of sera for cell culture are bovine fetal blood (FBS), calf (CS), horse (HS) or human. FBS is the most widely used. Its functions are multiple: adhesion of the cells to a solid surface (via adhesion molecules such as fetuin, fibronectin, vitronectin), growth stimulation (growth factors, GF; cytokines; hormones), protection (antioxidants, antitoxins, proteins), buffer and nutrition. However, serum composition is not completely resolved since it is a very complex fluid, containing at least 3 000 different proteins (Omenn, 2005). Another point to consider is the quickly rising cost of serum, due to an increasing demand (500-600$/L) (Davis, 2002). Moreover, serum requires extensive quality control, it contains proliferation inhibitors, its composition varies from batch to batch, and it hinders the purification of cell culture products. Serum can also be contaminated by viruses, bacteria and prions (Jayme et al. 1988; Freshney, 2000). It is therefore advantageous to replace serum by a mixture of defined components that would not present similar problems. Serum-free media allow a better control of cell proliferation and differentiation and reduce the risk of contamination (Zimmerman et al. 2000). However, serum-free media are much more specific than serum-containing media, often only supporting the growth or differentiation of the cell type for which it has been developed. The corollary of this is therefore that most cell lineage will require the development of their own serum-free medium.

Although serum-free medium formulations for myoblast culture have previously been reported (Ham et al. 1988) or are commercially available (Skeletal muscle cell medium BULLETKIT™, CC-3160 from Lonza), the extent and rate of myoblast proliferation in these media remains much lower than in serum containing media. To this date, Applicant is not aware of any effective serum-free medium for myoblast expansion.

Consequently, the development of a safer, serum-free culture medium that would efficiently support the expansion of myoblasts and their precursors would significant and timely contribute to the advent of cellular therapy based on the use of these cells.

SUMMARY OF THE INVENTION

The present invention relates to a culture medium for cells of the myogenic lineage that is free of serum and/or any other undefined supplement. This serum-free culture medium allows the cells to proliferate at a rate that is similar to the one of cells cultured in a serum-containing medium. The present invention also relates to a method for culturing cells in vitro where the serum-free medium is used. The use of the cells cultured in the serum-free media in cellular therapy for muscle-associated conditions is also contemplated.

According to a first aspect, the present invention provides a culture medium for a cell of the myogenic lineage. In an embodiment, the culture medium comprises a basal medium and a cytokine or a combination of cytokines. Preferably, the culture medium is free of serum and allows the proliferation of the cell of the myogenic lineage at a similar rate than another cell of the myogenic lineage cultured in a standard medium containing serum. In an embodiment, the cell of the myogenic lineage is at least one of a muscular stem cell, a myoblast and a myoblast-derived cell. In another embodiment, the muscular stem cell can differentiate into a myoblast. In yet another embodiment, the myoblast-derived cell is at least one of a muscle cell, a satellite cell and a myocyte. In still another embodiment, the cell of the myogenic lineage is derived from a biopsy, is a mammalian cell and/or is a human cell. In an embodiment, the basal medium is at least one of Dulbecco's modified Eagles's medium (DMEM), advanced DMEM, BIOGRO™, SKGM®, Ham's F10, Ham's F12, Iscove's modified Dulbecco's medium, neurobasal medium, RPMI 1640 and MCDB120 medium. In another embodiment, the basal medium is a combination of Ham's F12, RPMI 1640 and MCDB120 and, in a further embodiment, the proportion of Ham's F12, RPMI 1640 and MCDB120 is about 1:1:1. In an embodiment, the cytokine is a human cytokine. In still another embodiment, the cytokine is a recombinant cytokine. In yet another embodiment, the cytokine is at least one of a growth factor (GF) and an interleukin. In still another embodiment, the growth factor is at least one of a fibroblast growth factor (FGF), an epidermal growth factor (EGF) and an insulin-like growth factor (IGF). In yet another embodiment, the concentration of FGF in the culture medium is between about 1 and 20 ng/ml. In an embodiment, the FGF is at least one of FGF-1, FGF-2, FGF-4, FGF-5, FGF-6, FGF-7, FGF-8 and FGF-9. In still another embodiment, the concentration of EGF in the culture medium is between about 1 and 20 ng/ml. In yet another embodiment, the concentration of IGF in the culture medium is between about 1 and 50 ng/ml. In an embodiment, the IGF is at least one of IGF-1 and IGF-2. In still another embodiment, the concentration of interleukin in the culture medium is between about 0.1 to 20 ng/ml. In an embodiment, the interleukin is at least one of IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32 and IL-33. In yet another embodiment, the culture medium further comprises a supplement and, in yet another embodiment, the supplement is at least one of: i) a combination of insulin (at a concentration, for example, of 0.5 mg/ml), transferrin (at a concentration, for example, of 5 mg/ml) and selenite (at a concentration, for example, of 0.52 µg/ml) (ITS); ii) B27 medium supplement; iii) a combination of dexamethasone, insulin, EGF, fetuin and albumin; and iv) a combination of dexamethasone, bFGF, albumin and insulin. In still another embodiment, the concentration of ITS in the culture medium is between about 0.5 and 2.5% v/v. In yet another embodiment, the culture medium further comprises a lipid and, in still another embodiment, the lipid is at least one of arachidonic acid, cholesterol, DL-α-tocopherol acetate, linoleic acid, linolenic acid, myristic acid, oleic acid, palmitoleic acid, palmitic acid and stearic acid. In still another embodiment, the concentration of the lipid in the culture medium is between about 0.5 and 2.5% v/v.

In a second aspect, the present invention provides an in vitro method of culturing a cell of the myogenic lineage. The method can comprise contacting the cell of the myogenic lineage with the culture medium described herein thereby culturing said cell. In an embodiment, the cell of the myogenic lineage is at least one of a muscular stem cell, a myoblast and a myoblast-derived cell. In a further embodiment, the muscular stem cell can differentiate into a myoblast. In yet another embodiment, the myoblast-derived cell is at least one of a muscle cell, a satellite cell and a myocyte. In an embodiment, the method is performed for at least an hour, for at least a day, for at least a week or for at least a month. In an embodiment, the method reduces the lag phase of the cell of the myogenic lineage with respect to the lag phase of a cell of the myogenic lineage cultured in another serum-free media. In another embodiment, the method enables the long term expansion of the cell of the myogenic lineage. In still another embodiment, the initial concentration of the cell of the myogenic lineage in the culture medium is 10 000 cells/mL. In yet another embodiment, the method enables the cell of the myogenic lineage to retain its ability to form a myotube.

In a third aspect, the present invention provides a method of treating or alleviating a muscular deficiency in a subject in need thereof. In an embodiment, the method comprises contacting a cell of the myogenic lineage with the culture medium described herein; and implanting the cell previously obtained in the subject; thereby treating or alleviating the muscular deficiency in the subject. In an embodiment, the method comprises providing a cell of the myogenic lineage cultured by the method described herein and implanting the cultured cell obtained in the subject; thereby treating or alleviating the muscular-associated condition in the subject. In an embodiment, the subject is a human. In another embodiment, the muscular-deficiency is at least one of Duchenne muscular dystrophy, myocardial infarction, urethral sphincter insufficiency.

In a fourth aspect, the present invention provides the use of a cell of the myogenic lineage cultured in the culture medium described herein or prepared by the method described herein for the treatment or the alleviation of symptoms of a muscular deficiency in a subject. In an embodiment, the subject is a human. In another embodiment, the muscular deficiency is associated with at least one of Duchenne muscular dystrophy, myocardial infarction, urethral sphincter insufficiency.

In a fifth aspect, the present invention provides a cell of the myogenic lineage cultured in the culture medium described herein or prepared by the method described herein for the treatment or the alleviation of symptoms of a muscular deficiency in a subject. In an embodiment, the subject is a human. In another embodiment, the muscular deficiency is associated with at least one of Duchenne muscular dystrophy, myocardial infarction, urethral sphincter insufficiency.

BRIEF DESCRIPTION OF THE DRAWINGS

Having thus generally described the nature of the invention, reference will now be made to the accompanying drawings, showing by way of illustration, a preferred embodiment thereof, and in which.

DETAILED DESCRIPTION OF THE PREFERRED EMBODIMENT

Figure 1:
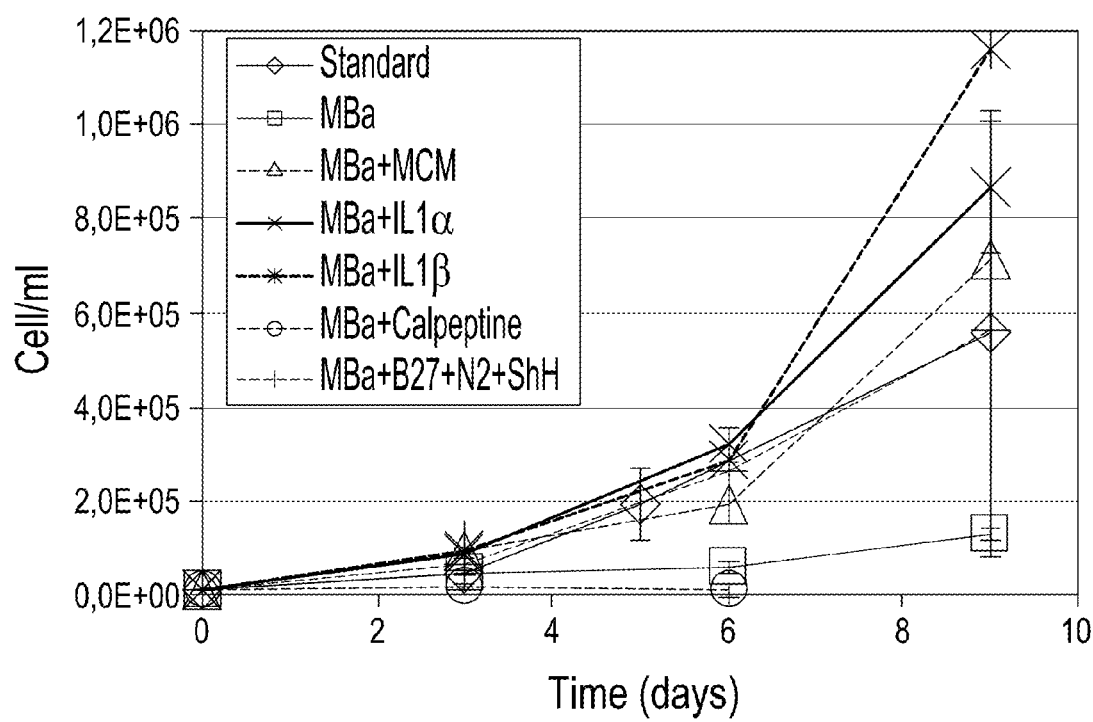
FIG. 1 compares the expansion of human myoblasts cultured in various media (◇, standard (STD) medium; □, first generation serum-free medium (MBa); Δ, MBa supplemented with macrophage conditioned medium (MCM); x, MBa supplemented with interleukin 1α (IL-1α); *, MBa supplemented with IL1β; ○, MBa supplemented with calpeptine; |, MBa supplemented with B27 supplement, N2 supplement and sonic hedgehog (ShH) during the course of a nine-day culture.

Broadly, the present application relates to a culture medium that enables the in vitro expansion of cells of the myogenic lineage (such as muscular stem cells, myoblasts and myoblast-derived cells) that is free of serum. The main advantages of this serum-free culture medium is its safety, the elimination of growth inhibitors contained in serum, a more consistent lot to lot medium composition, and easier approbation by regulating authorities for its use in clinical trials (Freshney 2005). The proposed culture medium allows cells to proliferate rapidly and to high concentration without an adaptation period. That period is often necessary to slowly adapt the cells by reducing progressively serum concentration. It also permits the rapid proliferation of cells to a high concentration if the cells are seeded at a low concentration (such as 10 000 cells/ml). Further, the serum-free medium does not stimulate the differentiation and fusion of myoblasts into myotubes. However, the serum-free medium allows cultured myoblasts to maintain their capacity to form myotubes in vitro when transferred into a differentiating medium. Consequently, it is contemplated that the cells cultured in the medium retain their ability to fuse to muscle fibers in vivo.

According to one aspect, the culture medium provided herein is for a cell of the myogenic lineage. As used herein, the term "cell of the myogenic lineage" refers to a cell capable of expressing genes and proteins specific to myoblasts or to a cell having a myoblastic phenotype. Myoblast-specific genes and proteins include, but are not limited to, MyoD, Myf5, MRF4, myogenin, Pax3, Pax7, desmin, creatine phosphokinase, muscle-specific myosin, Mind bomb 2, α-actin, troponin-I, actinin, MyHC, zeugmatin, titin, nebulin and MyBP-C. The myoblastic phenotype encompasses the ability of a myoblast to fuse to generate a muscle cell and form myotubes or to de-differentiate into a satellite cell.

Cells of the myogenic lineage include muscular stem cell, myoblast and myoblast-derived cells. Muscular stem cells are known to differentiate into myoblasts. Myoblast-derived cells include, but are not limited to, muscle cells and satellite cells. Muscle cells or muscle fibers have an elongated, cylindrical shape and are multinucleated. The nuclei of these muscles are located in the peripheral aspect of the cell (Totsuka 1987), just under the plasma membrane, which vacates the central part of the muscle fiber for myofibrils. In the heart, the muscle cells are also referred to as a myocytes (also known as myocardial cells). Each myocardial cell contain myofibrils, which are long chains of sarcomeres, the contractile units of the cell. Myocytes show similar pattern to skeletal muscle cells, unlike multinucleated skeletal cells, myocytes contain only one nucleus. Satellite cells are small mononuclear progenitor cells with very little cytoplasm and can be found in the mature muscle. They are usually located between the basal lamina and sarcolemma of individual muscle fibers. Satellite cells are able to differentiate and fuse to augment existing muscle fibers and to form new fibers. In undamaged muscle, the majority of satellite cells are quiescent. In response to a mechanical strain, satellite cells become activated; they initially proliferate as skeletal myoblasts before undergoing myogenic differentiation. Satellite cells express a number of distinctive genetic markers such as Pax7 and Pax3. Activated satellite cells also express myogenic transcription factors, such as Myf5 and MyoD. Differentiated satellite cells express muscle-specific filament proteins such as desmin.

The cells that can be cultured in the serum-free medium are preferably those of the myogenic lineage. These cells include, but are not limited to, commercially available cell lines (such as the $C_2C_{12}$ cell line) as well as primary cultures of cells. In the latter, the cells can be obtained from a tissue biopsy (such as a biopsy of a healthy muscle tissue) or can be derived from stem cells (such as those present in blood (such as cord blood), skin, muscles, etc). Cells of the myogenic lineage of any origin (such as mammalian cells, murine cells and human cells) can be successfully cultured in the serum-free medium. The serum-free medium could be used for the culture of adherent cells and non-adherent cells.

As herein described, the serum-free culture medium allows the proliferation of the cells of the myogenic lineage at a rate similar to the rate that would be obtained with a standard medium with serum. As used herein, the expression "similar rate of proliferation" refers to a rate of proliferation that is either not statistically different or superior to cells cultured in standard serum-containing medium. As shown below in the Examples, commercially available serum-free culture media (such as the SKGM® medium from Lonza) for cells of the myogenic lineage do not enable the growth and proliferation of the cells at a rate similar to the standard medium with serum. The culture medium proposed herein provides a tangible advantage when compared to the existing media in the art.

The culture medium contains at least two components (i) a basal medium and (ii) a cytokine. The basal medium provides a source of consumable energy for the cells, a source of amino acids, minerals, vitamins, salts, trace elements. The basal medium can be either a single medium or a combination of more than one medium. Basal medium contemplated for incorporation into the serum-free medium can be, for example, Dulbecco's Modified Eagle's Medium (DMEM), advanced DMEM, BIOGRO™, SKGM®, Ham's F10, Ham's F12, Iscove's modified Dulbecco's medium, neurobasal medium, RPMI 1640 and/or MCDB120. In a preferred embodiment, the basal medium is a combination of Ham's F12, RPMI 1640 and MCDB120 media. In another embodiment, the ratio between these three basal media is approximately 1:1:1.

The second component of the culture medium is a cytokine. As it is known in the art, cytokines play a crucial role in the activation, growth, proliferation and differentiation of myoblasts. For example, when the muscle is injured, the first phase of muscular repair is necrosis of damaged parts and the activation of the inflammatory response (Charge and Rudnicki 2004). The latter is characterized by the secretion of cytokines by damaged fibers and the cells of the immune system. These cytokines activate quiescent satellite cells who then enter the cellular cycle and proliferate. This activation triggers myogenesis, a series of complex events which involves the differentiation of satellite cells into muscle precursor cells, and the fusion of the later to form muscle fibers. Finally, once the muscle repaired, the inflammatory response fades and the satellite cells return to their quiescent state (Miller et al. 2000; Muntoni et al. 2002).

In order to develop the serum-free culture medium, Applicant has investigated which cytokines could become valuable potential additives to the basal medium. Cytokines are often specific to a cell type, play several important roles in the body, regulate many processes, influence cellular survival, growth and differentiation, etc. In myoblasts, cytokines are also involved in the assembly of the actin cytoskeleton and the mobility of the cells (Kurek et al. 1998; Cooper and Hausman, 2007). Generally, cytokines have the following characteristics:

They have different effects on different cell or tissue, due to the difference in expression of their respective receptors on any given cell type (Schlessinger and Ullrich, 1992; Fitzgerald et al. 2001).

Different cytokines can induce similar reactions since several receptors share similar intracellular signaling pathways. These cytokines are thus known as redundant.

The concentration of cytokines needed to induce an effect is very low, (in the ng/ml range) since receptor affinity for its ligand is generally very high and binding often leads to signal amplification.

Cytokines are part of complex reaction networks, an act in either positive or negative synergy with other cytokines. Multiple cytokines also act in sequence to lead to the complete response (Fitzgerald et al. 2001; Hancock, 2005; Lewin, et al. 2007).

New cytokines are discovered each year, but until now, 80 are known and their mass varies between 10 and 70 kDa (Hancock 2005). Cytokines were originally described as soluble polypeptides used as communication agents between lymphoid cells. However, cytokine definition is now broader and designate any protein which acts on proliferation or differentiation, whereas "growth factor" (GF) is used specifically to define cytokines with a positive effect on cellular division.

Several GF are secreted by macrophages during the immune response and by skeletal muscle cells in an autocrine manner. Generally, they act as progression factors of the cell cycle that prevent the formation of myotubes, but would also contribute to the maturation of muscle fibers and the migration of myoblasts (Kinoshita et al. 1995; Allen et al. 2003; Lafreniere et al. 2004).

Until now, around 50 GF have been identified and several affect muscle cells, such as family members of the fibroblast growth factors (FGFs), epidermal growth factors (EGF, HB-EGF, TGFα), insulin-like growth factor (IGFs), transforming growth factors (TGFs), bone morphogenic factors (BMPs), hepatocyte growth Factor (HGF), leukemia inhibitory factor (LIF), platelet-derived growth factor (PDGFs), vascular-endothelial growth factor (VEGF), macrophage colony-stimulating factor (M-CSF) and nerve growth factor (NGF) (Floss et al. 1997; Fitzgerald et al. 2001). Some GF receptors are expressed in several types of cells (FGF, EGF, IGF-1) whereas others, such colony-stimulating factor (CSF) and the NGF, are more specific (Schlessinger and Ullrich, 1992).

Interleukins are the principal group of hematopoietic cytokines. They allow communication between cells of the immune and inflammatory systems and control the growth and the differentiation of several cell types. The macrophages and the monocytes produce several types of interleukins that could play an important role in muscle skeletal cell proliferation. To our knowledge, very few project studied the effects of interleukins on muscular cell proliferation, which makes their investigation interesting.

The most studied hematopoietic cytokines are the leukemia inhibitory factor (LIF) of the IL-6 family, IL-1 (α and β) and TNFα. LIF specifically stimulates the proliferation and the survival of myoblasts, without supporting those of fibroblasts. TNFα pushes satellite cells to enter and to remain in the cell cycle, induced IL-6 production, stimulates angiogenesis, increases migration and acts as mitogen for rat myoblasts (Austin et al. 1992; White et al. 2001; Ferrara et al. 2003; Li, 2003; Torrente et al. 2003; Langen et al. 2004; Chevrel et al. 2005). Finally, IL-1 is a cytokine which modulates cellular proliferation by the induction and the inhibition of others cytokines and is a precursor of the inflammatory response (Wang et al. 2005). For example, IL-1β induces the production of IL-6, arachidonic acid, human growth hormone, nitric oxide and certain inflammatory proteins, such as collagenase and elastase, in myoblasts (Mizel, 1989; Fitzgerald et al. 2001; Adams et al. 2002; Chevrel et al. 2005). Moreover, it would prevent IGF-1 from promoting protein synthesis, down-regulating myogenin by the means of ceramide production, a secondary messenger (Broussard et al. 2004; Strle et al. 2004).

In the serum-free medium, many cytokines (such as those listed above) can be added. They can be in a purified form, derived from humans or animals or they can be obtained through recombinant technology. Many cytokines are readily available commercially. In one embodiment, the cytokines can either be one or more growth factors (such as FGF, EGF, BMP, TGFβ or IGF), and/or one or more interleukins (such as IL-1 to IL-33), and/or one or more hematopoietic cytokines (such as ILs, EPO or M-CSF). The concentration of the growth factors varies but it is usually in a range between about 1 to 100 ng/ml. The concentration of interleukin also varies, but it is usually in a range between about 0.1 to 100 ng/ml. When selecting the cytokine to be added in the serum-free medium, one should take care in selecting a cytokine or a combination of cytokines that it will allow the proliferation of the cells of the myogenic lineage, limit cell death or senescence and enable the cells to retain their ability to differentiate into muscle cells.

The culture medium could also comprise a supplement. This supplement will allow the proliferation of the cells of the myogenic lineage, limit cell death or senescence and/or enable the cells to retain their ability to differentiate into muscle cells. Such supplements can include, but are not limited to (i) a combination of insulin, transferrin and selenite (also known as ITS), (ii) a commercially available B27 supplement (content listed in Table 5, as well as in Brewer et al. 1993), (iii) a combination of dexamethasone, insulin, EGF, fetuin and albumin (also known as Ham's modified additive supplement described in Ham et al. 1988, as well as in Table 1) and/or (iv) a combination of dexamethasone, insulin, bFGF and albumin (Table 2). The concentration of these supplement will vary depending on their intended use. Usually, the concentration of a ITS 100× solution ranges between 0.005% and 2.5% (v/v).

Antimicrobial compounds (such as antibiotics) can also be added to the medium to prevent microbial growth during culture, inasmuch as they do not alter cell proliferation, cell death and/or ability to fuse or differentiate.

Lipids can be useful in the culture of cells and can be added to the serum-free medium. Examples of useful lipids includes arachidonic acid, cholesterol, DL-α-tocopherol acetate, linoleic acid, linolenic acid, myristic acid, oleic acid, palmitoleic acid, palmitic acid and stearic acid. The concentration of lipids in the culture medium is usually between 0.05% and 5% (v/v). Lipids added in the serum-free medium should allow the proliferation of the cells of the myogenic lineage, limit cell death or senescence and enable the cells to retain their ability to differentiate into muscle cells.

Surfactants can also be added in the serum-free medium, as long as they allow the proliferation of the cells of the myogenic lineage, limit cell death or senescence and enable the cells to retain their ability to differentiate into muscle cells. Several surfactants can be used, for example pluronic F-68® and TWEEN® (such as TWEEN 80®).

The present application also relates to a method of culturing a cell of the myogenic lineage. In an embodiment, this method comprises the step of contacting the cell with the culture medium described herein. Any cell of the myogenic lineage (such as those described herein) can be used in this method. The method contemplates the culture of cells on a surface (such as a culture appropriate container or a bead) and the culture of non-attached cells (such as cell lines that form free-floating aggregates in culture). The method can be used for short-term culture period (such as about an hour or more than an hour or about a day or more than one day), mid-term culture period (such as about a week or more than a week) or long-term culture period (such as about a month or more than a month). As described above, the culture medium enables the proliferation of cells at a rate similar of those cultured in a serum-containing medium. Consequently, the method provided herewith does not alter the proliferating rate of cells when compared to traditional methods using serum. The method also has the advantage of limiting cell differentiation in culture while retaining the cell's ability to differentiate when they are placed in a differentiating culture medium or in vivo.

Another advantage of the culture method presented herewith is that it can be used in the scaling up of large volumes of culture (for example, between 1 to 100 liters).

Because the culture medium described herein is free of serum, it can be safely use for the ex vivo expansion of cells that will be implanted or grafted in a patient in need thereof. As described above, the treatment of muscle deficiencies using ex vivo cultured cells is already known in the art. However, because the culture medium described herewith enables the in vitro proliferation of cells of the myogenic lineage while retaining the cultured cell's ability to differentiate (e.g. fuse), the present invention provides a new alternative for providing cells for therapy of a muscular deficiency. It is known in the art that the success of such cellular therapy is linked to the number of cells that can be transferred to the patient. Because the culture medium presented herewith (as well as its corresponding method of using the culture medium) does not contain serum (a risk factor for a potential microbial/prion infection) and enables the proliferation of cells in vitro, it is contemplated that it could be successfully used in cellular therapy.

As such, the present application also relates to the treatment or the alleviation of symptoms of a muscular deficiency in a subject in need thereof. The method comprises contacting a cell of the myogenic lineage with the culture medium described herein or culturing a cell of the myogenic lineage according the method described herein. The cell is then implanted in a subject in need thereof to treat or alleviate the symptoms associated to a muscular deficiency. As used herein, the term "muscular deficiency" refer to a significant reduction in muscle mass in a subject, modifying abilities to maintain posture, movement and ultimately vital functions. Muscular deficiency are, for example, any muscular dystrophy (such as Duchenne, Becker, limb girdle, congenital, facioscapulohumeral, myotonic, oculopharyngeal, distal, and Emery-Dreifuss dystrophy), myocardial infarction and urethral sphincter insufficiency.

The present application also contemplates the use of the serum-free culture medium and cells cultured therein for the treatment or the alleviation of symptoms of a muscular deficiency or dysfunction.

The present invention will be more readily understood by referring to the following examples which are given to illustrate the invention rather than to limit its scope.

Example I

Methodology Used

Cell culture and media. Myoblasts used in the following examples were derived from three digested human muscular biopsies, BB13, H49 and H51. BB13 cells were separated from fibroblasts following the protocol described in Belles-Iles et al., 1993, and were therefore at least 95% desmin positive (DakoCytomation clone DE-R-11, code M0724) and 95% NKH1 (Beckman-Coulter). H49 and H51 cells were not purified and contained >50% desmin positive-cells. The cells were initially cultured in MCDB120 basal medium (Hyclone SH3A11704.01), complemented with 15% fetal bovine serum (FBS, Hy-Clone SH30396.03, lot KPF21343) and the modified Ham's supplement (refer to Table 2 below). This medium was also used as a positive control, standard (STD) medium. This STD medium is the one presently used to support myoblast proliferation for current clinical trials of in vivo muscular treatments.

The serum-free medium (also referred to as LOBSFM or LOB-SFM) is composed of a mixture of three basal media. The three basal media are Ham F12 (Invitrogen 11765-054), RPMI1640 (Invitrogen 21870-076) and MCDB120 (Hyclone SH3A1704.01, lot # AQE23666) combined in a 1:1:1 ratio. The compositions of those three basal media are described in Table 4 and Table 5. This mixture is supplemented with six growth factors/cytokines and seven additives (Table 3), Ham's growth supplement cocktail (Table 1) and its modified version (Table 2).

The commercially available medium from Lonza, (SKGM®, Lonza CC-3160) is composed of a basal medium (SKGM®) and an additive mixture (BULLETKIT™) similar in composition to the Ham's supplement (Table 1): insulin (CC-4025N), rhEGF (CC-4017N), BSA (CC-4160N), fetuin (CC-4140N), GA-1000 (CC-4081N) and dexamethasone (CC-4150N).

TABLE 1

Culture medium supplement proposed by Ham (Ham et al. 1988)

| Additives | Concentration |
|---|---|
| Dexamethasone | 0.39 μg/L |
| Insulin | 0.18 mg/ml |
| EGF | 10 ng/ml |
| Bovine Albumin | 0.5 mg/ml |
| Fetuin | 0.5 mg/ml |

TABLE 2

Modified culture medium supplement used in the standard medium

| Additives | Concentration |
|---|---|
| Dexamethasone | 0.39 μg/L |
| Insulin | 5 μg/ml |
| bFGF | 10 ng/ml |
| Bovine albumin | 0.5 mg/ml |

TABLE 3

Cytokines and additives mixture added in LOBSFM

| Cytokines//Additives | Concentration |
|---|---|
| bFGF | 4 ng/ml |
| FGF4 | 4 ng/ml |
| EGF | 4 ng/ml |
| IGF1 | 4 ng/ml |
| IL1α | 4 ng/ml |
| IL1β | 4 ng/ml |
| BSA | 0.5 mg/ml |
| Fetuin | 0.5 mg/ml |
| Fibronectin | 5 μg/ml |
| Dexamethasone | 0.39 μg/ml |
| ITS | 1 X |
| Lipids | 1 X |
| B27 | 1 X |

TABLE 4

Amino acid content of Ham F12, RPMI 1640 and MCDB120 media

| Basal media Amino acids (mg/L) | Ham's F12 (mg/L) | RPMI 1640 (mg/L) | MCDB120 (mg/L) | LOBSFM (mg/L) |
|---|---|---|---|---|
| Glycine | 7.5 | 10 | 2.25 | 6.58 |
| L-Alanine | 8.9 | | 2.67 | 3.86 |
| L-Alanine-L-Glutamine | 217 | | | 72.33 |
| L-Arginine | | 200 | | 66.67 |
| L-Arginine hydrochloride | 211 | | 210.67 | 140.56 |
| L-Asparagine | 13 | 50 | | 21 |
| L-Asparagine e-H$_2$O | | | 15.01 | 5 |
| L-Aspartic acid | 13.3 | 20 | 13.31 | 15.54 |
| L-Cysteine hydrochloride-H$_2$O | | | 35.13 | 11.71 |
| L-Cystine 2HCl | 36 | 65 | | 33.67 |
| L-Glutamic Acid | 14.7 | 20 | 4.41 | 13.04 |
| L-Glutamine | | 300 | 1461.5 | 587.17 |
| L-Histidine | | 15 | | 5 |
| L-Histidine hydrochloride-H$_2$O | 21 | | 41.93 | 20.98 |
| L-Isoleucine | 4 | 50 | 65.58 | 39.86 |
| L-Leucine | 13.1 | 50 | 131.17 | 64.76 |
| L-Lysine hydrochloride | 36.5 | 40 | 181.65 | 86.05 |
| L-Methionine | 4.5 | 15 | 29.84 | 16.45 |
| L-Phenylalanine | 5 | 15 | 33.04 | 17.68 |
| L-Proline | 34.5 | 20 | 11.51 | 22 |
| L-Serine | 10.5 | 30 | 31.53 | 24.01 |
| L-Threonine | 11.9 | 20 | 35.73 | 22.54 |
| L-Tryptophan | 2.04 | 5 | 4.08 | 3.71 |
| L-Tyrosine | 5.4 | | 18.12 | 7.84 |
| L-Tyrosine disodium salt dehydrate | | 29 | | 9.67 |
| L-Valine | 11.7 | 20 | 117.15 | 49.62 |

TABLE 5

Vitamins, salts, trace elements, lipids and other additives contained in Ham F12, RPMI 1640 and MCDB120

| Basal media | Ham's F12 (mg/L) | RPMI 1640 (mg/L) | MCDB120 (mg/L) | LOBSFM (mg/L) |
|---|---|---|---|---|
| Vitamins | | | | |
| Biotin | 0.0073 | 0.02 | 0.00733 | 0.012 |
| Folic Acid | 1.3 | 1 | | 0.767 |

TABLE 5-continued

Vitamins, salts, trace elements, lipids and other additives contained in Ham F12, RPMI 1640 and MCDB120

| Basal media | Ham's F12 (mg/L) | RPMI 1640 (mg/L) | MCDB120 (mg/L) | LOBSFM (mg/L) |
|---|---|---|---|---|
| Folinic acid (5-formyl tetrahydrofolate-5$H_2$O) (Ca salt) |  |  | 0.602 | 0.201 |
| Niacinamide | 0.036 | 1 | 6.11 | 2.382 |
| D-Pantotheique acid (Hemi-Ca salt) |  |  | 23.82 | 7.94 |
| D-Calcium pantothenate | 0.5 | 0.25 |  | 0.25 |
| Pyridoxine hydrochloride | 0.06 | 1 | 2.056 | 1.039 |
| Riboflavin | 0.037 | 0.2 | 0.003764 | 0.08 |
| Thiamine hydrochloride | 0.3 | 1 | 3.373 | 1.558 |
| Cobalamine | 1.4 | 0.005 | 0.01355 | 0.473 |
| Choline chloride | 14 | 3 | 13.96 | 10.32 |
| i-Inositol | 18 | 35 | 18.016 | 23.672 |
| Para-Aminobenzoic Acid |  | 1 |  | 0.333 |
| Salts |  |  |  |  |
| $CaCl_2$—2$H_2$O | 44 |  | 235.23 | 93.08 |
| $Ca(NO_3)_2$—4$H_2$O |  | 100 |  | 33.33 |
| $MgCl_2$—6$H_2$O | 122 |  |  | 40.67 |
| MgSO4—7H2O |  |  | 246.38 | 82.13 |
| $MgSO_4$(anhyd) |  | 48.8 |  | 16.28 |
| KCl | 223.6 | 400 | 298.2 | 307.27 |
| $NaHCO_3$ | 1176 | 2000 | 1176 | 1450.67 |
| NaCl | 7599 | 6000 | 6430 | 6676.33 |
| $Na_2HPO_4$ (anhyd) | 142 | 800 |  | 314 |
| $Na_2HPO_4$—7$H_2$O |  |  | 134.04 | 44.68 |
| Traces elements |  |  |  |  |
| $(NH_4)_6Mo_7O_{24}$—4$H_2$O |  |  | 0.0037 | 0.0012 |
| $HNH_4VO_3$ |  |  | 0.0006 | 0.0002 |
| $CuSO_4$—5$H_2$O | 0.003 |  | 0.0025 | 0.0017 |
| $FeSO_4$—7$H_2$O | 0.834 |  | 0.834 | 0.556 |
| $MnSO_4$—5$H_2$O |  |  | 0.00024 | 0.00008 |
| $NiCl_2$—6$H_2$O |  |  | 0.00007 | 0.00002 |
| $H_2SeO_3$ |  |  | 0.00387 | 0.00129 |
| $Na_2SiO_3$—9$H_2$O |  |  | 2.842 | 0.947 |
| $ZnSO_4$—7$H_2$O |  |  | 0.086 | 0.029 |
| Lipids |  |  |  |  |
| Linoleic acid | 0.1 |  |  | 0.028 |
| Lipoic acid | 0.2 |  |  | 0.067 |
| Others |  |  |  |  |
| Adenine |  |  | 0.135 | 0.045 |
| D-Glucose | 1802 | 2000 | 1000 | 1601 |
| Glutathione (reduced) |  | 1 |  | 0.33 |
| Hypoxanthine | 4 |  |  | 1.33333 |
| Phenol Red | 1.2 | 5 | 1.242 | 2.481 |
| Putrescine 2HCl | 0.2 |  | 0.00016 | 0.05372 |
| Sodium pyruvate | 110 |  | 110.04 | 73.35 |
| Thymidine | 0.7 |  | 0.024 | 0.241 |

Proliferation Assays and Designs of Experiments (DOE).

A frozen aliquot of 1-3×10⁶ myoblasts was thawed and diluted to 2×10⁵ cells/ml in STD medium in a 75 cm² tissue culture T-flask and incubated at 37° C. in a humidified, 5% $CO_2$ atmosphere. After approximately five days, the culture reached 80% confluence, at which point the cells were trypsinized, rinsed and centrifuged three times with phosphate buffer saline (PBS), and inoculated in cell culture multiwell plates (either 6 or 24 wells) at 10 000 cells/ml in the different culture media. No adaptation of cells for serum-free conditions was made before the experiments. Media change was performed every two to three days and cells were counted using a hemacytometer.

Immunostaining Assays.

Cells recuperated from an enzymatic digestion of a muscular biopsy form a heterogeneous cellular population, even when myoblast enrichment is performed. An efficient myoblast culture medium will not only allow extensive and rapid proliferation of any cells, but will also specifically favor myoblast proliferation. Consequently, characterization of cell population at different points in time during their expansion is important. To do so, immunostaining was performed, and the degree of expression of myoblast specific markers was assessed either by microscopy or flow cytometry. The markers used in this study were desmin (DakoCytomation clone DE-R-11, code M0724), NKH-1 (NKH1-1-RD1/NCAM/CD56; Beckman Coulter 6603067) and myosin heavy chain (MHC; MF20 (Iowa Hybridoma Bank)). Desmin is a highly specific marker for activated satellite cells and myogenic precursors. The anti-desmin antibody stains the intermediate filaments of the cytoskeleton (Freshney 2005). NCAM (neural cell adhesion molecule) is a glycoprotein found at high concentration on the plasma membrane of myoblasts and progenitors of muscular skeletal cells (Nomura, Ashihara et al. 2007), but also on neurons and on natural killer cells (NK). NCAM is thus a little less specific than desmine for myoblasts. MHC indicates the formation of myotubes. DAPI (Sigma D8417) was also used to color the nucleus. In order to perform desmin and MHC staining, cells were rinsed and agitated three times with PBS, incubated 5 minutes each time with fresh PBS; cells were fixed with a solution of ethanol 95%, incubated 10 minutes, and discarded; a solution of PBS supplemented with 10% FBS was added, let to incubate one hour, and discarded; a solution of PBS supplemented with 10% FBS and the antibody (anti-desmin or anti MHC) was added, incubated one hour, and discarded; cells were rinsed and agitated three times in PBS, 5 minutes each time with fresh PBS; a solution of PBS supplemented with 10% FBS and the labeled secondary antibody (with ALEXAFLUOR 488™ or ALEXAFLUOR 546™) was added, incubated one hour, and discarded; cells were rinsed and agitated three times in PBS, 5 minutes each time with fresh PBS; and DAPI was added on the last rinse. At least 500 cells are counted for each condition to allow for proper result accuracy.

Fusion Assay.

Culture medium was removed from the culture well when 80%-90% confluence was reached and it was replaced by a differentiation medium. The differentiation medium was composed of RPMI1640/F12/MB1 completed only with ITS (10 μg/ml insulin, 5.5 μg/ml transferring, 6.7 ng/ml sodium selenite). Under these conditions, normal myoblasts usually differentiate and fuse to form myotubes within three to four days.

Reverse-Transcriptase Polymerase-Chain-Reaction (RT-PCR).

RT-PCR was used to probe the transcriptome of receptors and autocrine factors expressed by myoblasts, as well as the growth factors expressed by macrophage, since it has been reported that macrophage conditioned medium promotes myoblast proliferation (Cantini et al. 1994; Massimino et al. 1997; Caroleo et al. 2001; Cantini et al. 2002; Chazaud et al. 2003; Tidball, 2005). BB13 cells were used for myoblast expression profiling, since they are a 95-100% pure myoblast population. A monocyte/macrophage cell line (ATCC CRL-9855) was also used to study macrophage expression. The ligands of myoblast receptors were also surveyed. Primer for each of these genes were found in the scientific literature and synthesized.

TABLE 6

Primers sequences for myoblast receptors, ligands and muscle-specific genes.

| Target mRNA (NCBI Ref. No.) | Forward | Reverse | Size (bp) Temp. (° C.) |
|---|---|---|---|
| β-actin (NM_001101.2) | AGCCTCGCCTTTGCCGA (SEQ ID NO: 1) | CTGGTGCCTGGGGCG (SEQ ID NO: 2) | 175 (54) |
| activin-RIIA (NM_001616.3) | TACTGCTGCAGATGGACCTG (SEQ ID NO: 3) | AGCTCCAGTTCAGAGTCCC (SEQ ID NO: 4) | 389 (60) |
| BMP-R1α (NM_004329.2) | GCAATTGCTCATCGAGACC (SEQ ID NO: 5) | CGAAGGTGTAGATGTCAGCC (SEQ ID NO: 6) | 232 (58) |
| BMP-R1β (NM_001203.1) | GCAGCACAGACGGATATTGT (SEQ ID NO: 7) | TTTCATGCCTCATCAACACT (SEQ ID NO: 8) | 630 (56) |
| BMP-R2 (NM_001204.5) | ACGGGAGAGAAGACGAGCCT (SEQ ID NO: 9) | CTAGATCAAGAGAGGGTTCG (SEQ ID NO: 10) | 694 (60) |
| C-MET (NM_000245.2) | GGTCAATTCAGCGAAGTCCT (SEQ ID NO: 11) | TTCGTGATCTTCTTCCCAGTG (SEQ ID NO: 12) | 242 (56) |
| COL1 (NM_000088.3) | GGAAACAGACAAGCAACCCAAACT (SEQ ID NO: 13) | GGTCATGTTCGGTTGGTCAAAGATAA (SEQ ID NO: 14) | 142 (55) |
| Desmin (NM_001927.3) | TCTGAAGCTGAGGAGTGGTA (SEQ ID NO: 15) | CTTCTTGGTATGGACCTCAG (SEQ ID NO: 16) | 465 (60) |
| DHH (NM_021044.2) | GTTGTAAGGAGCGGGTGAAC (SEQ ID NO: 17) | GCCAGCAACCCATACTTGTT (SEQ ID NO: 18) | 184 (58) |
| EGF (NM_001963.2) | GGTCAATGCAACCAACTTCA (SEQ ID NO: 19) | GGCATTGAGTAGGTGATTAG (SEQ ID NO: 20) | 383 (52) |
| EGF-R (NM_005228.3) | ATGTCCGGGAACACAAAGAC (SEQ ID NO: 21) | TTCCGTCATATGGCTTGGAT (SEQ ID NO: 22) | 351 (58) |
| EPO (NM_000799.2) | GATAAAGCCGTCAGTGGCCTTC (SEQ ID NO: 23) | GGGAGATGGCTTCCTTCTGGG (SEQ ID NO: 24) | 76 (60) |
| EPOR (NM_000121.2) | CCTGACGCTCTCCCTCATCC (SEQ ID NO: 25) | GCCTTCAAACTCGCTCTCTGG (SEQ ID NO: 26) | 130 (60) |

TABLE 6-continued

Primers sequences for myoblast receptors, ligands and muscle-specific genes.

| Target mRNA (NCBI Ref. No.) | Forward | Reverse | Size (bp) Temp. (° C.) |
|---|---|---|---|
| FGF-1 (NM_033136.1, NM_033137.1, NM_000800.2) | CATGGCTGAAGGGGAAATCAC (SEQ ID NO: 27) | AATCAGAAGAGACTGGCAGGGG (SEQ D NO: 28) | 363 (64) |
| FGF-2 (NM_002006.4) | TCACCACGCTGCCCGCCTTGC (SEQ ID NO: 29) | CAGTTCGTTTCAGTGCCACAT (SEQ ID NO: 30) | 375 (62) |
| FGF-3 (NM_005247.2) | TTGGAGATAACGGCAGTGGA (SEQ ID NO: 31) | CTCCAGGTTATCCGGGCTCT (SEQ ID NO: 32) | 438 (60) |
| FGF-5 (NM_004464.3, NM_033143.2) | GCTGTGTCTCAGGGGATTGTAGGAATA (SEQ ID NO: 33) | TATCCAAAGCGAAACTTGAGTCTGTA (SEQ ID NO: 34) | 434 (65) |
| FGF-7 (NM_002009.2) | ACCCGGAGCACTACACTATAATGC (SEQ ID NO: 35) | TTATTGCCATAGGAAGAAAGTGGG (SEQ ID NO: 36) | 600 (68) |
| FGF-10 (NM_004465.1) | GAGATGTCCGCTGGAGAAAG (SEQ ID NO: 37) | ATTTGCCTCCCATTATGCTG (SEQ ID NO: 38) | 304 (60) |
| FGFR-1 (NM_023110.2, NM_015850.3, NM_023105.2, NM_023106.2, NM_023107.2, NM_023111.2) | AAGGTCCGTTATGCCACCT (SEQ ID NO: 39) | CAGGTTGTCTGGGCCAATC (SEQ ID NO: 40) | 297 (58) |
| FGFR-2 (NM_022970.2, NM_000141.3) | GGAAAAGAACGGCAGTAAAT (SEQ ID NO: 41) | GTAGTCTGGGGAAGCTGTAA (SEQ ID NO: 42) | 247 (56) |
| FGFR-3 (NM_000142.2, NM_022965.1) | GGGCCCCTTACTGGACACG (SEQ ID NO: 43) | GCCGGATGCTGCCAAACT (SEQ ID NO: 44) | 270 (58) |
| FGFR-4 (NM_002011.3, NM_022963.2, NM_213647.1) | CGCTGGCTTAAGGATGGA (SEQ ID NO: 45) | CTGCCCACAGCGTTCTCT (SEQ ID NO: 46) | 149 (56) |
| FLRG- follistatin- related gene (NM_005860.2) | ACCTGAGCGTCATGTACCG (SEQ ID NO: 47) | TGTGGCACGAGGAGATGTAG (SEQ ID NO: 48) | 198 (60) |
| GAPDH (NM_002046.3) | GCCAAGGTCATCCATGACAAC (SEQ ID NO: 49) | GTCCACCACCCTGTTGCTGTA (SEQ ID NO: 50) | 498 (60) |
| G-CSF (NM_172220.1, NM_172219.1, NM_000759.2) | AGCTTCCTGCTCAAGTGCTTAGAG (SEQ ID NO: 51) | TTCTTCCATCTGCTGCCAGATGGT (SEQ ID NO: 52) | 336 (72) |
| GM-CSF (NM_000758.2) | GTCTCCTGAACCTGAGTAGAGACA (SEQ ID NO: 53) | AAGGGGATGACAAGCAGAAAGTCC (SEQ ID NO: 54) | 286 (722) |
| GM-CSFRα (NM_172249.1, NM_172247.1, NM_172245.1, NM_006140.3, NM_172246.1) | CTTCTCTCTGACCAGCA (SEQ ID NO: 55) | ACATGGGTTCCTGAGTC (SEQ ID NO: 56) | 546 (60) |
| GM-CSFRβ (NM_000395.1) | TGGAGTGGCCTCTGGTTATG (SEQ ID NO: 57) | GGGAACTAGGGAGACAGACGAG (SEQ ID NO: 58) | 82 (62) |
| HB-EGF (NM_001945.1) | GGTGCTGAAGCTCTTTCTGGCTGC (SEQ ID NO: 59) | ATTATGGGAGGCCCAATCCTAGAC (SEQ ID NO: 60) | 754 (72) |

TABLE 6-continued

Primers sequences for myoblast receptors, ligands and muscle-specific genes.

| Target mRNA (NCBI Ref. No.) | Forward | Reverse | Size (bp) Temp. (° C.) |
|---|---|---|---|
| HGF (NM_000601.4, NM_001010932.1) | CTACACTGGATTGATCAACTAT (SEQ ID NO: 61) | AGTAGTTGTCTTAGGATTGTTG (SEQ ID NO: 62) | 443 (52) |
| IGF-1 (NM_000618.2) | AAATCAGCAGTCTTCCAACC (SEQ ID NO: 63) | CTTCTGGGTCTTGGGCATGT (SEQ ID NO: 64) | 395 (57) |
| IGF-1R (NM_000875.3) | CTGCTGATGTGTACGTTCCT (SEQ ID NO: 65) | TCAGGTTCATCTTTCACCAC (SEQ ID NO: 66) | 133 (56) |
| IGF-II (NR_003512.1, NM_000612.3, NM_001007139.3) | CCTGGAGACGTACTGTGCTA (SEQ ID NO: 67) | GGACTGCTTCCAGGTGTC (SEQ ID NO: 68) | 132 (56) |
| IGF-IIR (NM_000876.2) | GCTGTTTGTATGCACGACTT (SEQ ID NO: 69) | TGCTCTGGACTCTGTGATTT (SEQ ID NO: 70) | 142 (56) |
| IHH (NM_002181.2) | CTACGCCCCGCTCACAAAG (SEQ ID NO: 71) | GGCAGAGGAGATGGCAGGAG (SEQ ID NO: 72) | 376 (60) |
| IL-1α (NM_000575.3) | GTCTCTGAATCAGAAATCCTTCTATC (SEQ ID NO: 73) | CATGTCAAATTTCACTGCTTCATCC (SEQ ID NO: 74) | 421 (58) |
| IL-1β (NM_000576.2) | TGAACTGAAAGCTCTCCACC (SEQ ID NO: 75) | CTGATGTACCAGTTGGGGAA (SEQ ID NO: 76) | 297 (60) |
| IL-2γ (NM_000206.1) | GGAAGCCGTGGTTATCTCTGTT (SEQ ID NO: 77) | GGTGGGTTGAATGAAGGAAAGT (SEQ ID NO: 78) | 407 (58) |
| IL-2Rα (NM_000417.1) | ATCCCACACGCCACATTCAAAGC (SEQ ID NO: 79) | TGCCCCACCACGAAATGATAAAT (SEQ ID NO: 80) | 347 (58) |
| IL-2Rβ (NM_000878.2) | GCCCCCATCTCCCTCCAAGT (SEQ ID NO: 81) | AGGGGAAGGGCGAAGAGAGC (SEQ ID NO: 82) | 529 (66) |
| IL-3Rα (NM_002183.2) | ACCCACCAATCACGAACCTAAG (SEQ ID NO: 83) | GGTCACATTTCTGTTAAGGTCCC (SEQ ID NO: 84) | 74 (66) |
| IL-4 (NM_000589.2, NM_172348.1) | ACTCTGTGCACCGAGTTGACCGTAA (SEQ ID NO: 85) | TCTCATGATCGTCTTTAGCCTTTCC (SEQ ID NO: 86) | 300 (55) |
| IL-4Rα (NM_001008699.1, NM_000418.2) | TGCGTCTCCGACTACATGAG (SEQ ID NO: 87) | TGACTGCATAGGTGAGATG (SEQ ID NO: 88) | 385 (60) |
| IL-5 (NM_000879.2) | TGCCTACGTGTATGCCATCCC (SEQ ID NO: 89) | CTTGGCCCTCATTCTCACTGC (SEQ ID NO: 90) | 438 (60) |
| IL-5R (NM_000564.2, NM_175725.1, NM_175724.1, NM_175726.1, NM_175727.1, NM_175728.1) | CCCTGAGGACACGCAGTATT (SEQ ID NO: 91) | TGATCAAAGGGCCTGATAGC (SEQ ID NO: 92) | 198 (60) |
| IL-6 (NM_000600.2) | ATGAACTCCTTCTCCACAAGCGC (SEQ ID NO: 93) | GAAGAGCCCTCAGGCTGGACTG (SEQ ID NO: 94) | 628 (58) |
| IL-6R (NM_000565.2) | CATTGCCATTGTTCTGAGGTTC (SEQ ID NO: 95) | AGTAGTCTGTATTGCTGATGTC (SEQ ID NO: 96) | 251 (60) |
| IL-7 (NM_000880.2) | TCTAATGGTCAGCATCGATCA (SEQ ID NO: 97) | GTGGAGATCAAAATCACCAG (SEQ ID NO: 98) | 190 (60) |
| IL-7R (NM_002185.2) | TGCTCAAAATGGAGACTTGG (SEQ ID NO: 99) | GAGGGCCCCACATATTTCA (SEQ ID NO: 100) | 160 (60) |
| IL-10 (NM_000572.2) | TGAGAACCAAGACCCAGACA (SEQ ID NO: 101) | TCATGGCTTTGTAGATGCCT (SEQ ID NO: 102) | 182 (60) |

TABLE 6-continued

Primers sequences for myoblast receptors, ligands and muscle-specific genes.

| Target mRNA (NCBI Ref. No.) | Forward | Reverse | Size (bp) Temp. (° C.) |
|---|---|---|---|
| IL-11 (NM_000641.2) | ATGAACTGTGTTTGCCGCCTG (SEQ ID NO: 103) | GAGCTGTAGAGCTCCCAGTGC (SEQ ID NO: 104) | 270 (64) |
| IL-12 (NM_002187.2) | TCACAAAGGAGGCGAGGTTC (SEQ ID NO: 105) | TGAACGGCATCCACCATGAC (SEQ ID NO: 106) | 378 (62) |
| IL-13Rα1 (NM_001560.2) | AAGGAATACCAGTCCCGACA (SEQ ID NO: 107) | ACCAGGGAACCATGAAACAAG (SEQ ID NO: 108) | 457 (60) |
| IL-13Rα2 (NM_000640.2) | GTGAAACATGGAAGACCATC (SEQ ID NO: 109) | GTGAAATAACTGGATCTGATAGGC (SEQ ID NO: 110) | 454 (60) |
| IL-15 (NM_172174.1 NM_000585.2) | TCTTCATTTTGGGCTGTTTCA (SEQ ID NO: 111) | GTGAACATCACTTTCCGTATA (SEQ ID NO: 112) | 143 (60) |
| IL-15Rα (NM_002189.2 NM_172200.1) | CGCCAGGTGTGTATCCAC (SEQ ID NO: 113) | GTTTGCCTTGACTTGAGGTA (SEQ ID NO: 114) | 121 (60) |
| IL-17 (NM_002190.2) | TCCCCAGTTGATTGGAAGA (SEQ ID NO: 115) | AGTCAAACCTTCCTTCTTGGA (SEQ ID NO: 116) | 709 (56) |
| IL-17R (NM_014339.4) | GCTTCACCCTGTGGAACGAATC (SEQ ID NO: 117) | GGAGATGCCCGTGATGAACCA (SEQ ID NO: 118) | 329 (66) |
| IL-18 (NM_001562.2) | ACCTGGAATCAGATTACTTTG (SEQ ID NO: 119) | CCATACCTCTAGGCTGGCT (SEQ ID NO: 120) | 195 (60) |
| IL-20Rβ (NM_144717.2) | CCTTCAGCCAGACAGAATGTGT (SEQ ID NO: 121) | GCAAACAGGGCCAGTACCA (SEQ ID NO: 122) | 67 (60) |
| IL-21R (NM_021798.2 NM_181078.1 NM_181079.1) | TGTGGAGGCTATGGAAGAAGATATG (SEQ ID NO: 123) | GTGCACCCACCCATTTCTTG (SEQ ID NO: 124) | 105 (72) |
| IL-22 (NM_020525.4) | ACAACACAGACGTTCGTCTCATTG (SEQ ID NO: 125) | GAACAGCACTTCTTCAAGGGTGA (SEQ ID NO: 126) | 113 (58) |
| IL-22R1 (NM_021258.2) | CCTGAGCTACAGATATGTCACCAAG (SEQ ID NO: 127) | GGCTGGAAAGTCAGGACTCG (SEQ ID NO: 128) | 78 (58) |
| LIF (NM_002309.2) | GCCATACGCCACCCATGTCACAAC (SEQ ID NO: 129) | GTTGGGGCCACATAGCTTGTCCAG (SEQ ID NO: 130) | 153 (76) |
| LIFR (NM_002310.3) | GTGGCAGTGGCTGTCATTGTTGGAGTGGT (SEQ ID NO: 131) | TCATCTGCGGCTGGGTTTGGTATTTCTTC (SEQ ID NO: 132) | 365 (86) |
| M-CSF (NM_000757.3 NM_172210.1 NM_172211.1 NM_172212.1) | TTGGGAGTGGACACCTGCAGTCT (SEQ ID NO: 133) | CCTTGGTGAAGCAGCTCTTCAGCC (SEQ ID NO: 134) | 249 (72) |
| MRF4 (NM_002469.1) | GCTCGTGATAACGGCTAAGGAA (SEQ ID NO: 135) | CGATGGAAGAAAGGCATCGA (SEQ ID NO: 136) | 80 (60) |
| Myf5 (NM_005593.2) | ATGGACGTGATGGATGGCTGCCAGTT (SEQ ID NO: 137) | GCGGCACAAACTCGTCCCCAAATT (SEQ ID NO: 138) | 103 (60) |
| MyoD (NM_002478.4) | AGCACTACAGCGGCGACT (SEQ ID NO: 139) | GCGACTCAGAAGGCACGTC (SEQ ID NO: 140) | 264 (60) |
| Myogenin (NM_002479.4) | GACATCCCCCTACTTCTACC (SEQ ID NO: 141) | TCACGCTCCTCCTGGTTG (SEQ ID NO: 142) | 420 (58) |
| Myosin-HC (NM_005963.3) | TGTGAATGCCAAATGTGCTT (SEQ ID NO: 143) | GTGGAGCTGGGTATCCTTGA (SEQ ID NO: 144) | 751 (60) |

TABLE 6-continued

Primers sequences for myoblast receptors, ligands and muscle-specific genes.

| Target mRNA (NCBI Ref. No.) | Forward | Reverse | Size (bp) Temp. (° C.) |
|---|---|---|---|
| Myostatin (NM_005259.2) | GGAAACAATCATTACCATGC (SEQ ID NO: 145) | ATCCATAGTTGGGCCTTTAC (SEQ ID NO: 146) | 129 (56) |
| NGF (NM_002506.2) | AGCTTTCTATCCTGGCCACA (SEQ ID NO: 147) | GATCCTGAGTGTCTGCAGCTT (SEQ ID NO: 148) | 344 (59) |
| p75 (NGF receptor) (NM_002507.1) | CCAGAGGGAGAAAAACTCCA (SEQ ID NO: 149) | CTGCACAGACTCTCCACGAG (SEQ ID NO: 150) | 371 (59) |
| PAX7 (NM_002584.1 NM_013945.1) | CAAGATTCTTTGCCGCTACC (SEQ ID NO: 151) | TTCAGTGGGAGGTCAGGTTC (SEQ ID NO: 152) | 390 (55) |
| PDGF-A (NM_033023.3 NM_002607.4) | CCCCTGCCCATTCGGAGGAAGAG (SEQ ID NO: 153) | TTGGCCACCTTGACGCTGCGGTG (SEQ ID NO: 154) | 227 (62) |
| PDGF-B (NM_002608.1 NM_033016.1) | GATCCGCTCCTTTGATGATC (SEQ ID NO: 155) | GTCTCACACTTGCATGCCAG (SEQ ID NO: 156) | 435 (60) |
| PDGFRα (NM_006206.3) | ATCAATCAGCCCAGATGGAC (SEQ ID NO: 157) | TTCACGGGCAGAAAGGTACT (SEQ ID NO: 158) | 891 (60) |
| PDGFRβ (NM_002609.3) | AATGTCTCCAGCACCTTCGT (SEQ ID NO: 159) | AGCGGATGTGGTAAGGCATA (SEQ ID NO: 160) | 688 (58) |
| PTC2-Hh receptor (NM_003738.3) | CTGGCTTCGTGCTTACTTCC (SEQ ID NO: 161) | CGGGTGTGAGGATGTTCTCT (SEQ ID NO: 162) | 287 (58) |
| SCF (NM_003994.4 NM_000899.3) | CTCCTATTTAATCCTCTCGTC (SEQ ID NO: 163) | TACTACCATCTCGCTTATCCA (SEQ ID NO: 164) | 177 (60) |
| sEPOR (NM_000121.2) | TGATTGGCTCAGTTCCACCAG (SEQ ID NO: 165) | AGGTTGCTCAGCACACACTC (SEQ ID NO: 166) | 128 (60) |
| SSH (NM_000193.2) | CGGAGCGAGGAAGGGAAAG (SEQ ID NO: 167) | TTGGGGATAAACTGCTTGTAGGC (SEQ ID NO: 168) | 262 (58) |
| TGFβ-1 (NM_000660.3) | ACCAACTATTGCTTCAGCTC (SEQ ID NO: 169) | TTATGCTGGTTGTACAGG (SEQ ID NO: 170) | 197 (55) |
| TGFβ-R1 (NM_004612.2) | TCGTCTGCATCTCACTCAT (SEQ ID NO: 171) | GATAAATCTCTGCCTCACG (SEQ ID NO: 172) | 342 (54) |
| TGFβ-2 (NM_003238.1) | CTGTCCCTGCTGCACTTTTGT (SEQ ID NO: 173) | TCTTCCGCCGGTTGGTCTGTT (SEQ ID NO: 174) | 227 (58) |
| TGFβ-3 (NM_003239.1) | CCTTTCAGCCCAATGGAGAT (SEQ ID NO: 175) | ACACAGCAGTTCTCCTCCAA (SEQ ID NO: 176) | 259 (57) |
| TGFβ-R2 (NM_003242.5 NM_001024847.2) | GCGGGAGCACCCCTGTGTC (SEQ ID NO: 177) | CCCGAGAGCCTGTCCAGATGC (SEQ ID NO: 178) | 213 (62) |
| TGFβ-R3 (NM_003243.2) | AATCTGGGCCATGATGCAG (SEQ ID NO: 179) | ACTGCTGTTTTCCGAGGCT (SEQ ID NO: 180) | 286 (57) |
| TNF (NM_000594.2) | TCAGCCTCTTCTCCTTCCTG (SEQ ID NO: 181) | TGAAGAGGACCTGGGAGTAG (SEQ ID NO: 182) | 324 (60) |
| TNFR-1 (NM_001065.2) | ACCAAGTGCCACAAAGGAAC (SEQ ID NO: 183) | CTGCAATTGAAGCACTGGAA (SEQ ID NO: 184) | 263 (55) |
| TNFR-2 (NM_001066.2) | TTCGCTCTTCCAGTTGGACT (SEQ ID NO: 185) | CACCAGGGGAAGAATCTGAG (SEQ ID NO: 186) | 349 (55) |

TABLE 6-continued

Primers sequences for myoblast receptors, ligands and muscle-specific genes.

| Target mRNA (NCBI Ref. No.) | Forward | Reverse | Size (bp) Temp. (° C.) |
|---|---|---|---|
| TrkA-NGF receptor (NM_001012331.1 NM_002529.3 NM_001007792.1) | CAATGTCACCAGTGACCTCAA (SEQ ID NO: 187) | TGAACTCGAAAGGGTTGTCC (SEQ ID NO: 188) | 401 (59) |

Cellular RNA was 1) purified with TRIZOL®(Gibco 15596), 2) reverse transcribed and 3) amplified. 1) RNA isolation was done according to the manufacturer instructions (GIBCO). Briefly, 1E6 cells were mixed with 1 ml of TRIZOL® and incubate at room temperature for 5 minutes. Then, 200 μl/ml TRIZOL® of chloroform was added and mixed vigorously for 15 seconds and incubated 3 minutes at room temperature. The mixture was centrifuged for 15 minutes at 12 000 g. The aqueous phase containing RNA was recuperated and 500 μl/ml of TRIZOL™ of isopropanol for 15 seconds was added at room temperature to allow the precipitation of RNA. The mixture was incubated 10 minutes at room temperature and centrifuged at 12 000 g for 10 minutes. The supernatant was removed and rinsed with 1 ml/ml TRIZOL® of a 75% ethanol/25% distilled $H_2O$ solution, agitated on vortex few seconds, and centrifuged 5 minutes at 7 500 g. Then, briefly dry RNA samples were solubilized in distilled $H_2O$ (~40 μl). Total RNA was quantified and assayed for purity with a spectrophotometer (Beckman Coulter DU 650), where a minimum ratio $A_{260/280}>1.6$ was considered valuable (samples were diluted 1/200 in TRIS-EDTA). 2) For reverse transcription (RT), a mixture of Oligo dt (2 μL at 10 μM), 5 mM of each dNTPs (2 μL), RNA (1 μg) and RNAse free water was use to complete volume to 17 μl. The mixture was heated to 65° C. for RNA denaturation and cooled on ice. 2 μl of 10× buffer and 1 μl de RT were added. Thermocycling of the samples at 42° C. for 60 minutes and at 70° C. for 15 minutes to inactivate the enzyme complete the RT phase. 3) The mixture for PCR reaction consisted of dNTPs (0.5 μl 25 mM), Taq polymerase (20 U/ml), Taq buffer 10× (5 μl), cDNA (2 μl), forward+reverse primers (2 μl each) and deonized, RNAse free water (complete to 50 μl). The cycling conditions were as follow: 1 cycle at 94° C. for 2 minutes; 35 cycles at 94° C. for 30 seconds, annealing temperature for 30 seconds and 72° C. for 45 seconds; 1 cycle at 72° C. for 10 minutes; 1 cycle at 4° C. for an indefinite period. Finally, the amplicons were run on agarose gels to evaluate their concentration and their approximate molecular weight.

Statistics.

Calculations were performed using Matlab software and a p-value of 0.05 was deemed sufficient to recognize a significant effect.

Example II

Comparison of Seven Different Culture Media

The capacity of seven different culture media to support myoblast expansion was compared with second passage (P2) H49 cells. The cells were cultured as described in Example I and were inoculated in 24-well plasma treated plates (Sarstedt 83.1836, 500 μL/well). Cells were cultured in either i) STD medium, or ii) a first generation serum-free medium developed in our lab (MBa, composition described in Table 7) without any other additives, or additioned with either iii) a macrophage conditioned medium (obtained from the supernatant of a macrophage culture (ATCC CRL-9855) in DMEM supplemented with ITS, 48 hours following a stimulation with LPS), iv) IL-1α, v) IL-1β, vi) calpeptine or vii) with a combination of B27 (refer to Table 8 below), N2 and sonic hedgehog (ShH). As shown in FIG. 1, at culture day nine, four additives (MCM, IL-1α, IL-1β, or a combination of B27, N2 and ShH) significantly improved the proliferation of myoblasts compared to MBa alone. However, calpeptine appeared to act as a proliferation/expansion inhibitor.

TABLE 7

Composition of MBa medium

| Additives | Concentration | units |
|---|---|---|
| BSA | 0.5 | mg/ml |
| Fetuin | 0.5 | mg/ml |
| ITS | 1X | |
| Lipid | 1X | |
| Dexamethasone | 0.39 | μg/ml |
| bFGF | 5 | ng/ml |
| EGF | 5 | ng/ml |
| IGF-1 | 20 | ng/ml |
| PDGF-BB | 5 | ng/ml |
| FGF-4 | 10 | ng/ml |
| RPMI 1640 | ⅓ | — |
| F12 | ⅓ | — |
| MCDB 120 | ⅓ | — |

TABLE 8

Composition of B27 (Brewer et al. 1993)

| | |
|---|---|
| Biotin | Selenium |
| L-carnitine | T3 (triodo-1-thyronine) |
| Corticosterone | DL-a-tocopherol (vitamin E) |
| Ethanolamine | DL-a-tocopherol acetate |
| D(+)-galactose | Bovine albumin |
| Glutathione (reduced) | Catalase |
| Linoleic acid | Insulin |
| Linolenic acid | Superoxide dismutase |
| Progesterone | Transferrin |
| Putrescin | Retinyl acetate |

Example III

Comparison of Cell Expansion in Standard and Serum-Free Media

Figure 2:
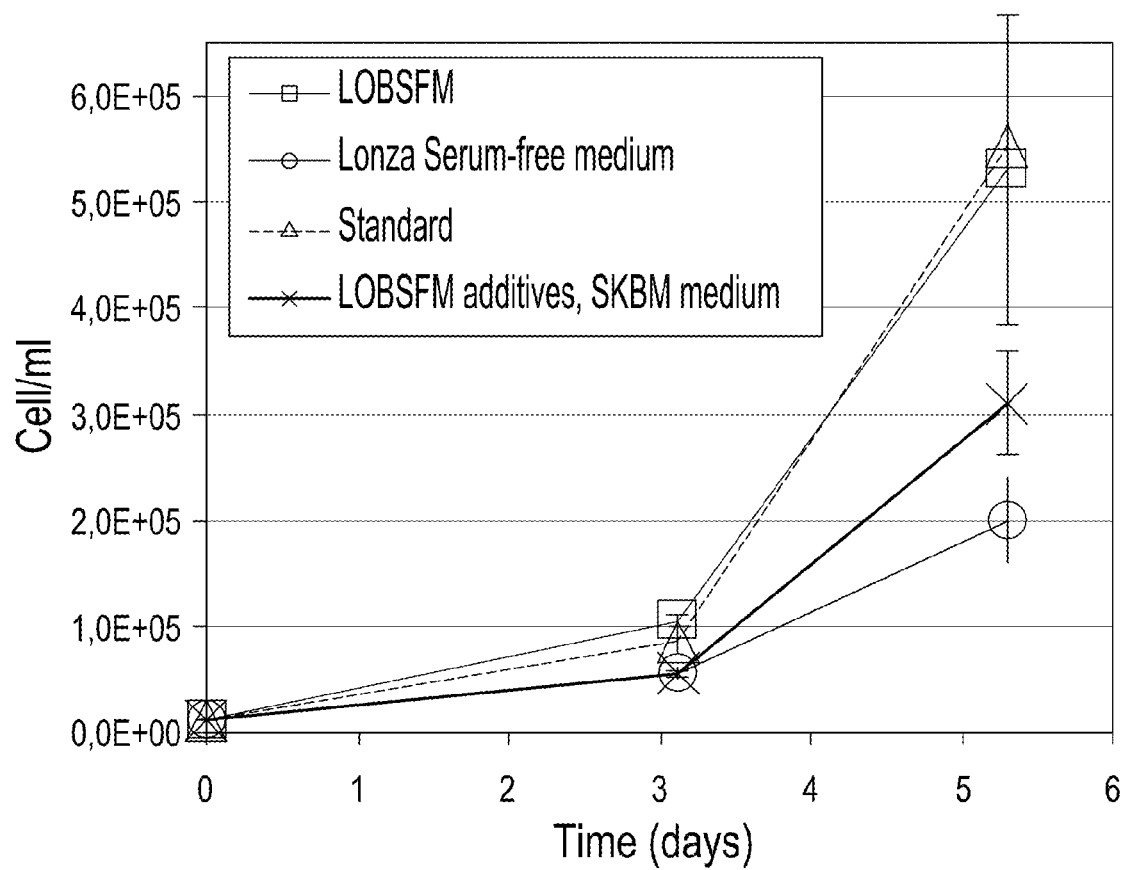
FIG. 2 compares the expansion of human myoblasts cultured in various media (□, optimized serum-free medium (LOBSFM); ○, Lonza serum-free medium composed of the basal medium SKBM® supplemented with BULLETKIT™ additives; Δ, standard medium; x, SKBM® medium supplemented with the LOBSFM additives for five days.

LOBSFM was compared to a serum-free medium commercially available from Lonza (SKGM® +BULLETKIT®) and with the standard medium (STD). BB13 cells in $P_4$ were cultured as described in Example I. The cells were inoculated in 24-well plasma treated plates (Sarstedt 83.1836, 500 µL/well) and cultured in either standard medium, SKGM® serum-free medium completed with the BULLETKIT™ additives, LOBSFM serum-free medium or SKGM® serum-free medium completed with LOBSFM additives. The cell were counted with a hemacytometer at three and five days post-plating. As shown in FIG. 2, cell expansions in the standard medium or in the LOBSFM serum-free medium are similar. However, the expansion of cells in the completed SKGM® serum-free medium or in the SKGM® medium with LOBSFM additives is less important than in the standard medium or in the LOBSFM medium.

Example IV

Comparison of Long Term Expansion of Cells in Standard and Serum-Free Media

Figure 3:
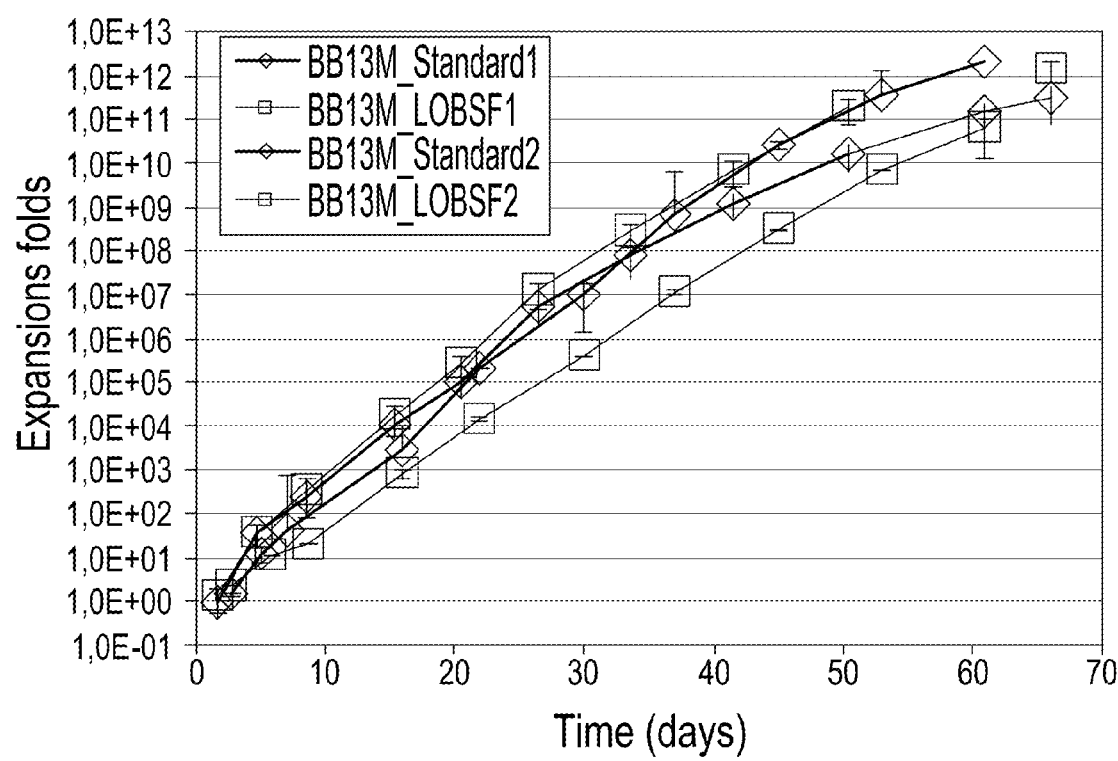
FIG. 3 compares the long-term expansion of BB13 cells in various media (◇, standard medium, duplicates 1 and 2; □, LOBSFM, duplicates 1 and 2) expressed in expansion folds in function of time (days).

The reproducibility of long term myoblast proliferation in the LOBSFM and the STD medium was also determined. BB13 cells in $P_4$ were cultured as described in Example I. The cells were trypsinized and inoculated in 24-well plasma treated plates (Sarstedt 83.1836, 500 µL/well) at a concentration of 10 000 cells/ml. The results shown in FIG. 3 represent two experiments carried out independently. The monitoring of cellular expansion accounts for the subsequent dilution of the culture, and is therefore expressed in expansion fold. As shown in FIG. 3, there is no statistical difference between cell expansions in STD medium or LOBSFM medium.

Example V

Comparison of Myoblast Specific Antigen and Gene Expressions for Cells Cultured in Standard and Serum-Free Medium In order to verify that the LOBSFM medium allowed the specific expansion of myoblasts, desmin and NKH-expression was imaged using antibodies. The expression of myoblast-specific antigen was performed on purified and non-purified myoblasts.

Figures 4A, 4B, 4C:
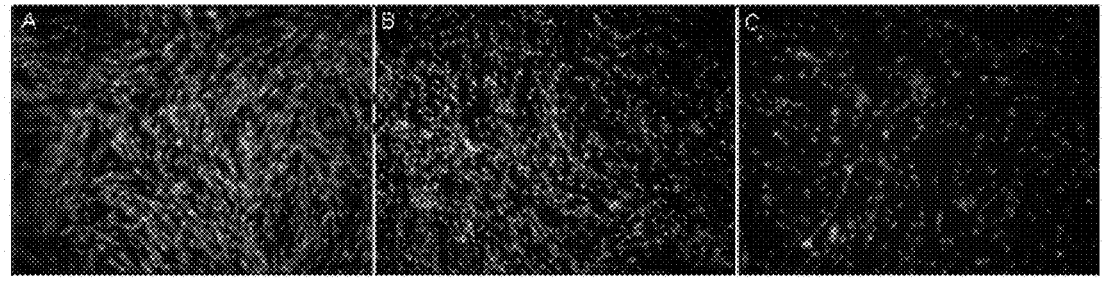
FIG. 4 shows micrographs of immunostained cells that proliferated in LOBSFM (A to F) and STD medium (G to I) with cell nucleic represented as dots; desmin represented as elongated structures in panels A-C, E and I, myosin heavy chain represented as elongated structures in panels D, F, G, H. The cells were cultured either for one week (D and G), two weeks (A), four weeks (B, E, H) or six weeks (C, F, I). Cells in boxes D to H were fixed and immunostained after a three-day incubation in the differentiation medium.
Figures 4D, 4E, 4F:
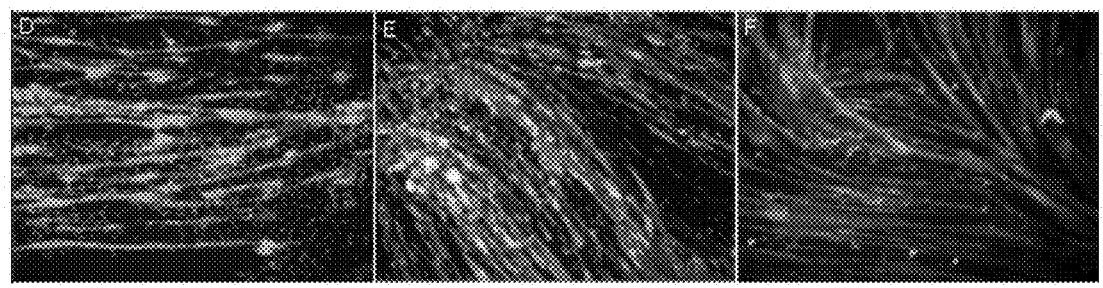
Figures 4G, 4H, 4I:
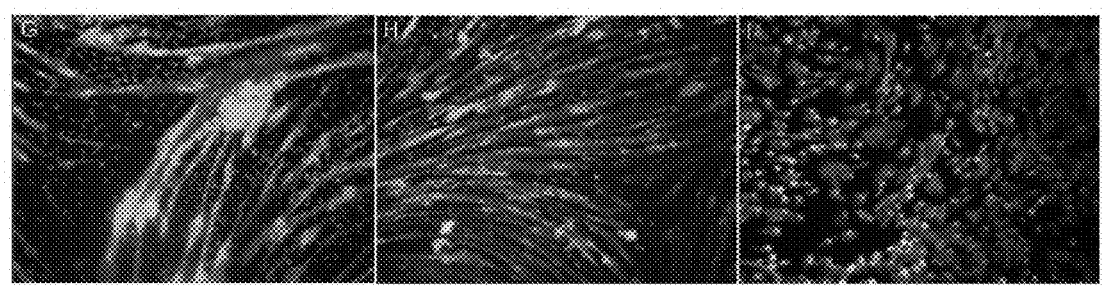
Figure 5A:
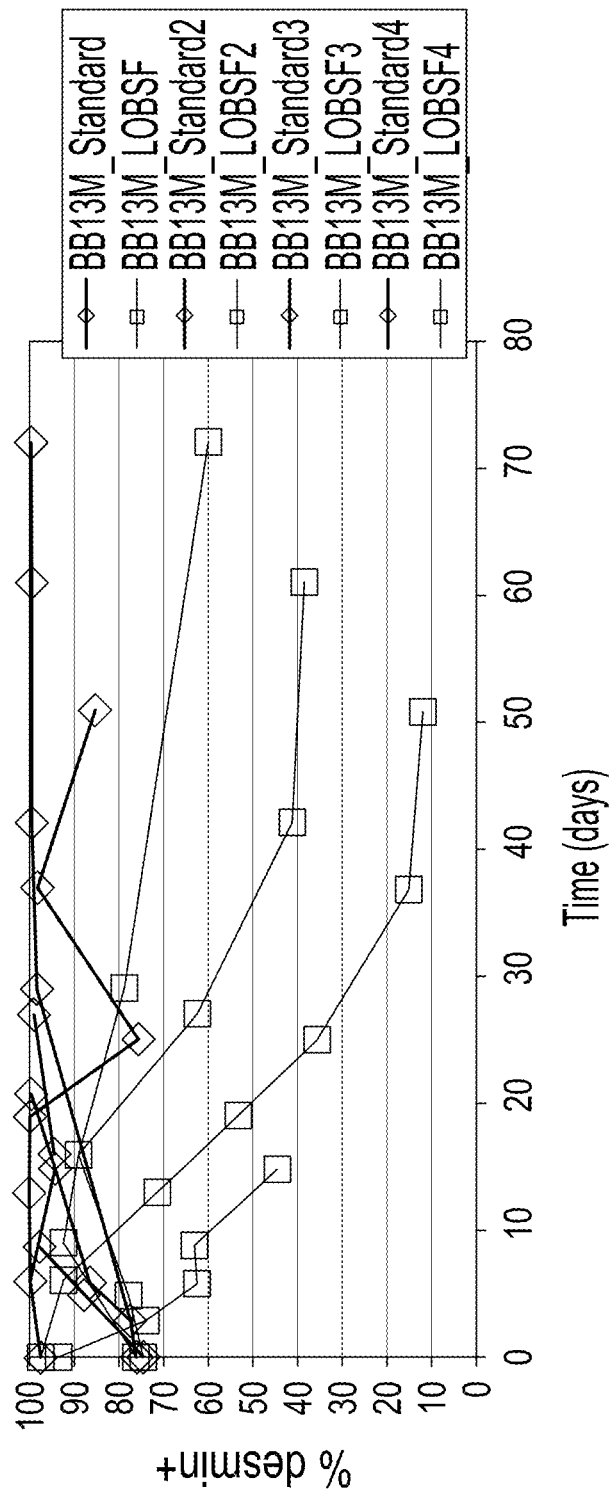
FIG. 5 illustrates the proportion of desmin-expressing cells from independent experiments for (A) BB13 cells in STD medium (◇) or LOBSFM (□); and (B) H49 (○) or H51 (Δ) cells in STD medium (solid line) or LOBSFM (broken line).
Figure 5B:
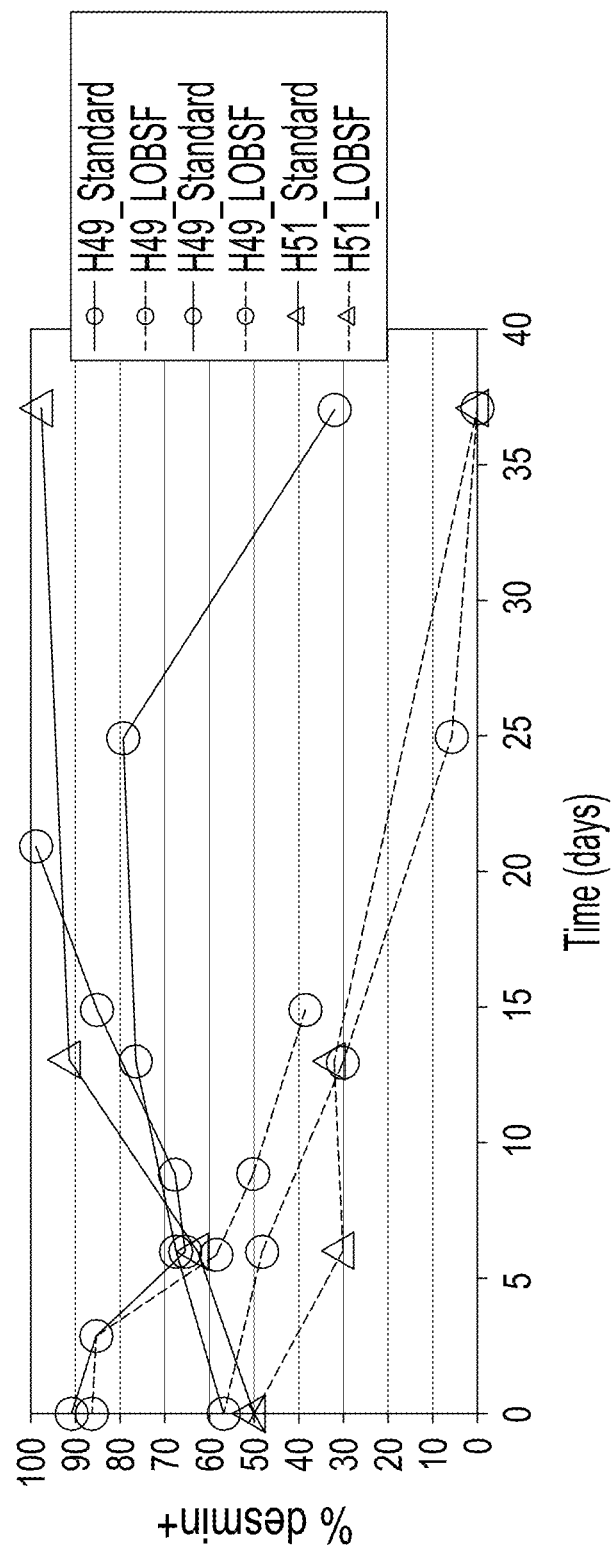
Figure 6A:
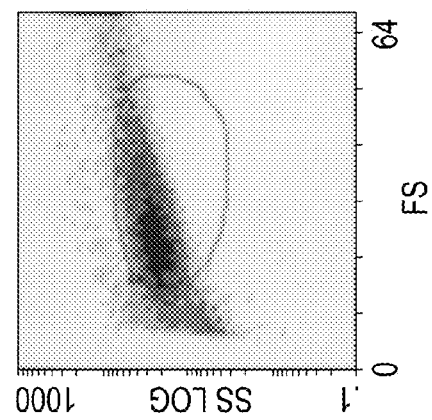
FIG. 6 shows flow cytometry results of a four weeks myoblast culture. (A) BB13 cellular counts against intensity for NCAM$^+$ cells cultured in LOBSFM (98.8%) or STD medium (96.9%). (B) H49 cellular counts against intensity for cells cultured in LOBSFM (left curve) or standard medium (right curve) as indicated by the arrows. (C) Side scatter against forward scatter for cells cultured in standard medium. (D) Side scatter against forward scatter for cells cultured in LOBSFM medium. The gated area in (C) and (D) represent cells analyzed for fluorescence.
Figure 6B:
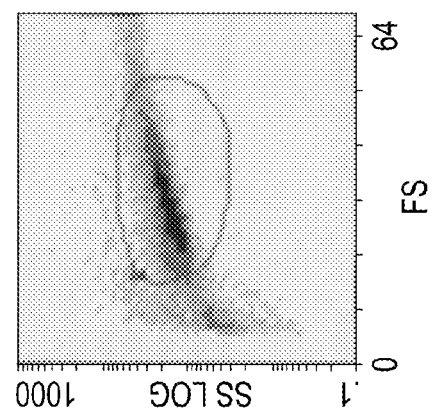
Figure 6C:
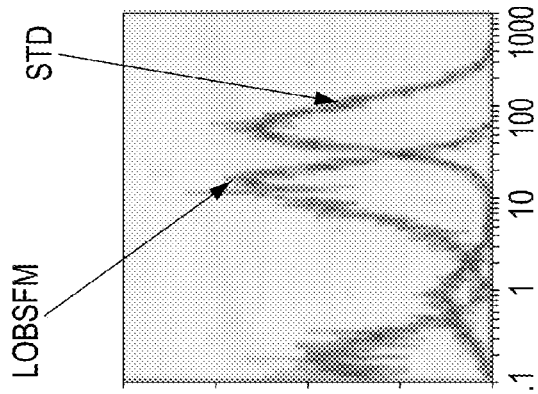
Figure 6D:
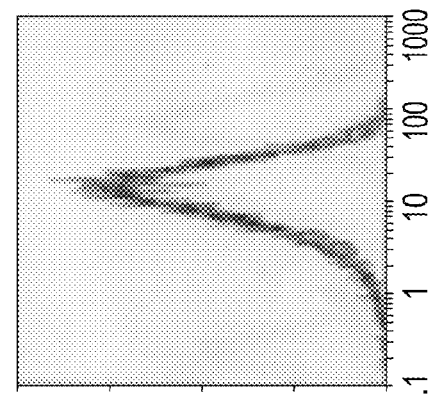

As shown in FIGS. 4 A to C and 5, the proportion of BB13 cells cultured in the LOBSFM serum-free medium that expressed detectable levels of desmin diminished progressively during the culture. This reduction in desmin expression was more pronounced for non-purified myoblasts (such as H49 and H51 cells, FIG. 5 B) than for purified myoblasts (BB13 cells, FIG. 5 A). In comparison, most of myoblasts cultured in the STD medium maintained high levels of desmin expression, for an extended culture period (six weeks, FIG. 4 I and FIG. 5). Nevertheless, when transferred in a differentiation medium, both BB13 cells expanded in STD medium or LOBSFM fused and expressed desmin similarly (FIGS. 4 B and E). This result indicates that culture in the LOBSFM medium does not alter the ability of the cells to differentiate to myotubes.

Figure 7:
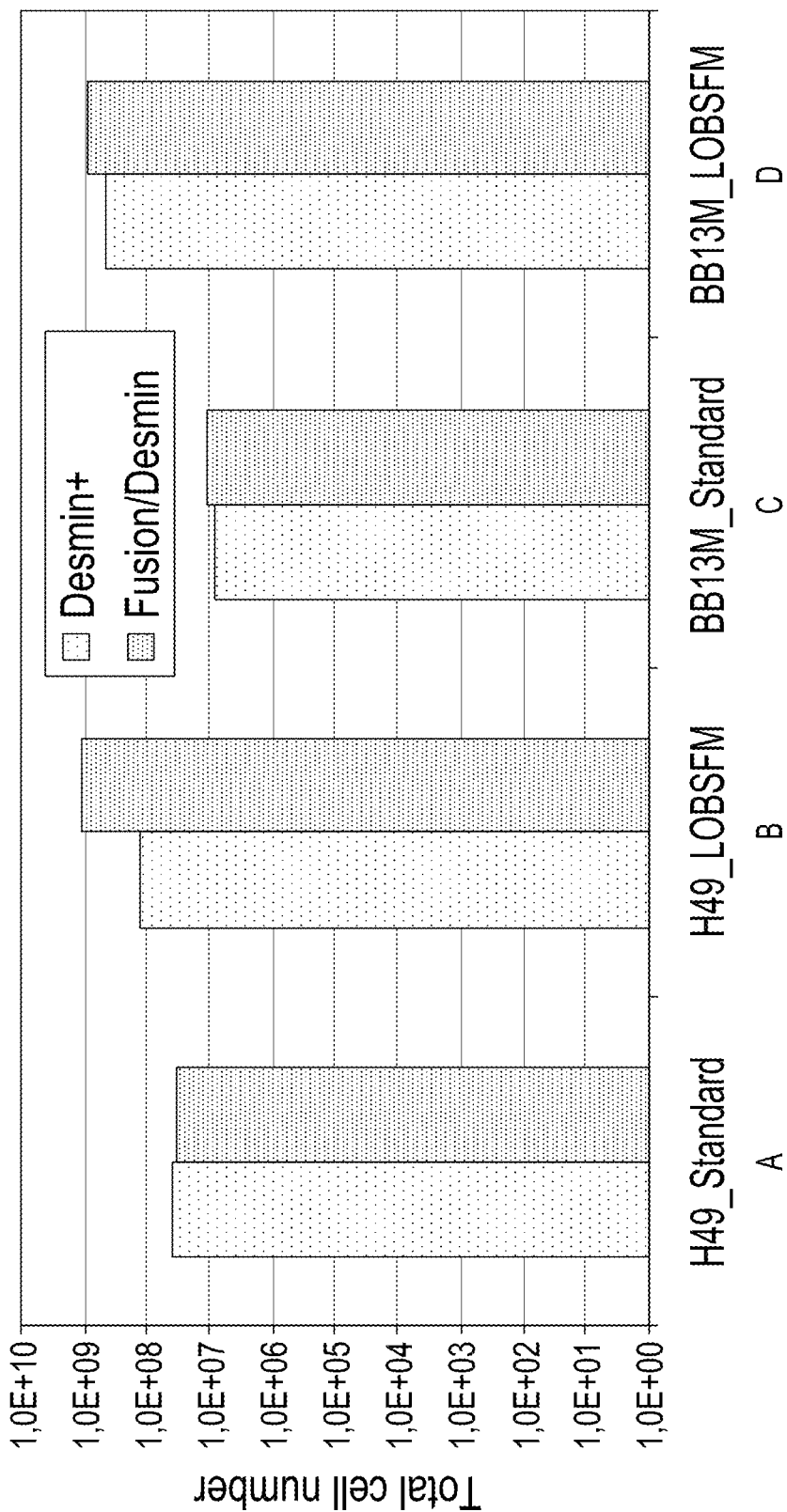
FIG. 7 illustrates the number of desmin-positive cells before (pale gray) and after (dark grey) fusion generated after a 25-day culture of H49 cells in STD medium (A) or LOBSFM (B) and of BB13 cells in STD medium (C) or LOBSFM (D).

As shown on FIGS. 4 G and H, BB13 cells first cultured in the STD medium fused efficiently when transferred to the differentiation medium (FIGS. 4 G and H). In comparison to cells cultured in the STD medium, BB13 cells first cultured for 25 days in the LOBSFM showed similar, or even higher, ability to form myotubes and fuse (FIG. 7). These results indicate that the LOBSFM medium supports the expansion/ proliferation of myoblasts while maintaining their myogenic potential, even though desmin expression can decrease during culture.

Myoblasts cultured for four weeks in LOBSFM or STD medium exhibited similar proportion of NKH-1 expressing BB13 cells (FIG. 6 A). However, although the expression levels were similar for BB13 cells, it was lower for non-purified H49 cells cultured in LOBSFM (FIG. 6 B).

Without wishing to be bound to theory, Applicant has hypothesized that this loss in desmin expression during culture could be caused by two phenomena: 1) the medium supports the proliferation of cells other than myoblasts or 2) certain cells can dedifferentiate during the culture. As indicated above, BB13 cells form a rather uniform population and express initially 95-100% desmin positive. Although phenomenon 1 can be observed during expansion of unpurified biopsies, it would be most unlikely in this case when culturing BB13 cells. Rather, it is most likely that BB13 cells dedifferentiate during culture in the LOBSFM. This dedifferentiation phenomenon has already been reported for other culture. For example, it was observed that the CNTF (ciliary neurotrophic factor) allowed myoblast clones (desmin$^+$) to form multipotent progenitors, having a self-renewal capacity and being able to form several cellular types, in particular neurons, smooth muscles cells and adipocytes. These cells proliferated during more than 20 passages without expressing the muscle regulatory factor (MRF) and it was possible to differentiate them back to the myogenic lineage afterward (Chen et al. 2005). In addition, it is also been shown that IL-1β blocked myogenin expression and the synthesis of several other proteins (Broussard et al. 2004). Finally, it was previously reported that TWEAK decreases not only the expression of myogenin and MyoD, but also of the actin filaments (Girgenrath et al. 2006). Consequently, the reduction of a marker expression during a culture, such as observed here for desmin in LOBSFM-cultured myoblasts, is not necessarily indicative of a loss in myogenesis capacity. The most important test for testing the functionality of myoblasts is a functional fusion in vitro assay to determine the potential of the cells to fuse together to form myotubes or a functional in vivo fusion assay in DMD patients. The added benefit of the in vitro assay is that it can be performed rapidly as a routine assay and is a good indicator of the in vivo situation.

The expression of several genes, specific or not for myoblasts, has also been quantified by RT-PCR as described in Example I. The RNA of $P_3$ BB13 cells cultured in STD medium for one passage has been isolated with TRIZOL®. The intensity of the RT-PCR product staining on an agarose gel has been listed in Table 9. The results obtained were used to select potential factors to be tested as additives, as well as interpret proliferation assay results previously presented.

TABLE 9

List of genes detected by RT-PCR and classified according to the bands on the agarose gel

| Target | Intensity |
|---|---|
| β-actin | + |
| BMP-R1α | +++ |
| C-MET | ++ |
| COL1 | +++ |
| DHH | ++ |
| EGF | +++ |
| EGF-R | +++ |
| EPOR | ++ |
| FGF-1 | +++ |

TABLE 9-continued

List of genes detected by RT-PCR and classified according to the bands on the agarose gel

| Target | Intensity |
|---|---|
| FGF-5 | ++ |
| FGFR-1 | +++ |
| FGFR-4 | ++ |
| GAPDH | +++ |
| GM-CSFRβ | + |
| IGF-1 | + |
| IGF-1R | ++ |
| IGF-II | +++ |
| IGF-IIR | + |
| IHH | + |
| IL-4Rα | + |
| IL-6R | + |
| IL-11 | ++ |
| IL-13Rα1 | +++ |
| IL-13Rα2 | + |
| IL-15Rα | + |
| IL-20Rβ | + |
| MRF4 | ++ |
| Myf5 | ++ |
| MyoD | +++ |
| Myostatin | ++ |
| NGF | + |
| p75 (NGF receptor) | ++ |
| PDGF-A | +++ |
| PDGFRα | + |
| PTC2 (Hh receptor) | ++ |
| sEPOR | ++ |
| SSH | +++ |
| TGFβ-1 | + |
| TGFβ-R1 | + |
| TGFβ-2 | +++ |
| TGFβ-3 | +++ |
| TGFβ-R2 | + |
| TGFβ-R3 | ++ |
| TNFR-1 | + |
| TrkA (NGF receptor) | + |

Example VI

Figure 8:
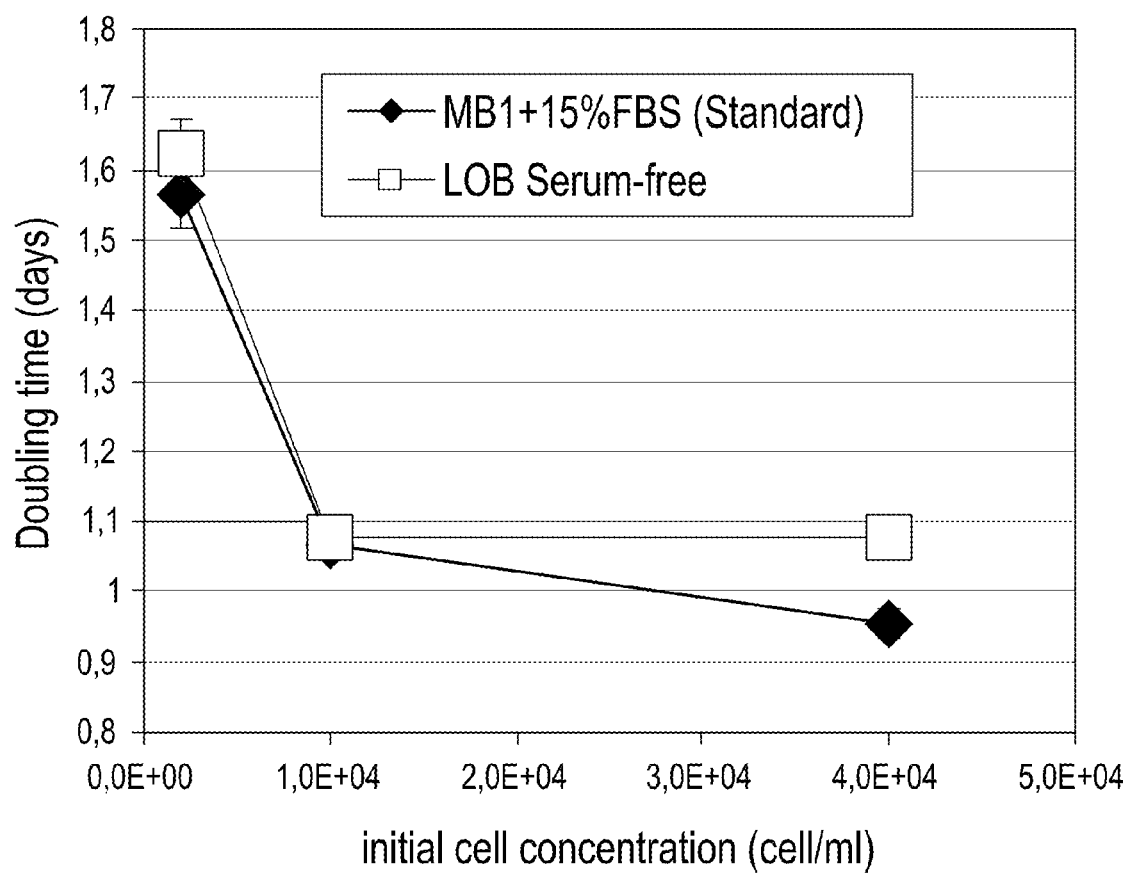
FIG. 8 illustrates the doubling time (in days) of BB13 cells cultured in standard (◇) or LOBSFM (□) medium in function of initial cellular concentration.

Comparison of Initial Seeding Density and Lag Phase for Cells Cultured in Standard and Serum-Free Medium In order to determine the minimal initial seeding cell density required to avoid a cell culture lag phase, $P_4$ BB13 cells were trypsinized and inoculated in 6-well plasma treated plates (Sarstedt 83.1839, 2 ml/well) at a concentration of either 2 000, 10 000 or 40 000 cells/ml in STD medium or LOBSFM. Cells were counted on the fifth day of culture. As shown in FIG. 8, the minimal initial cell concentration of 10 000 cell/ml allowed the culture to grow at a rate similar to the higher initial cell density No statistical difference in the results obtained with the two culture media (STD and LOBSFM) was observed.

Example VII

Figure 9:
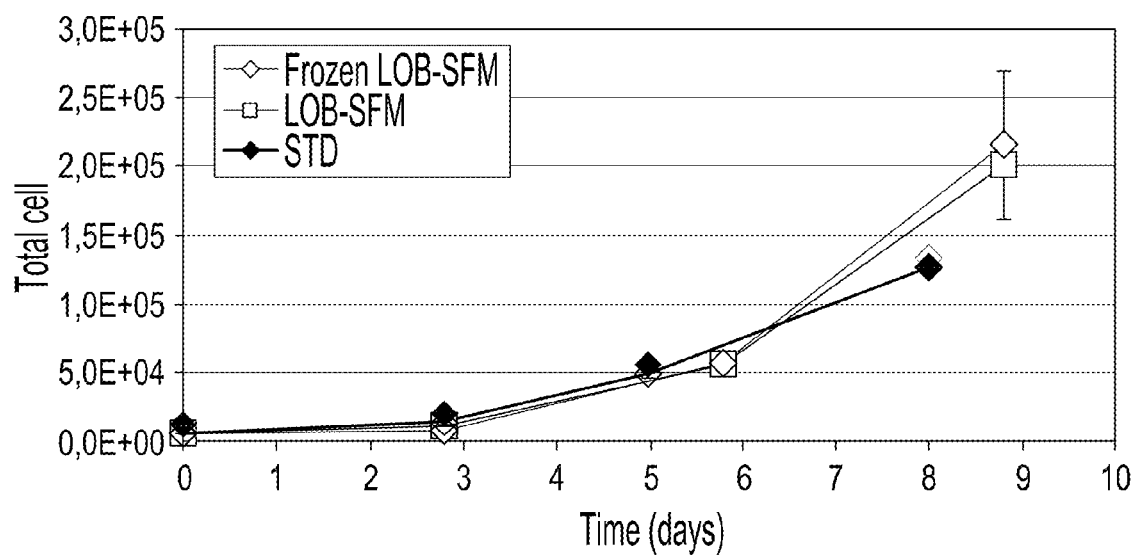
FIG. 9 compares the expansion of cells in function of days in culture of BB13 cells in standard (◇), fresh LOBSFM (□), or frozen/thawed LOBSFM (Δ) medium.
Figure 10:
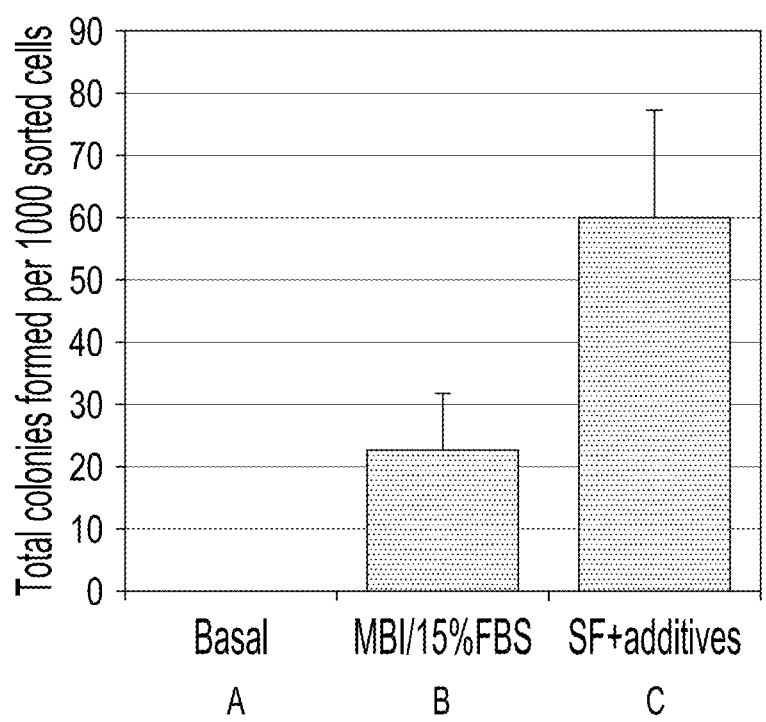
FIG. 10 illustrates the total colonies formed per 1 000 of FACS sorted mouse myogenic progenitor cells (gated for nucleated, live cells using Hoechst$^+$, and PI$^-$, and stained with CD31$^-$, CD45$^-$, sca1$^-$, and alpha7$^+$ antibodies were used) in (A) basal medium, (B) standard medium and (C) LOBSFM medium.

Comparison of a Freeze/Thaw Cycle on the Growth of Cells Cultured in Serum-Free Medium In order to determine the effect of LOBSFM freezing on cell growth, $P_4$ BB13 were trypsinised and inoculated in 24-well plasma treated plates (Sarstedt 83.1836, 500 μL/well) at an initial density of 10 000 cells/ml in either fresh STD medium or LOBSFM, or LOBSFM that has been frozen at −20° C. overnight, and then thawed. As shown in FIG. 9, a previously frozen LOBSFM does not significantly impact its capacity to expand myoblasts.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

REFERENCES

Adams, V., B. Nehrhoff, et al. (2002). "Induction of iNOS expression in skeletal muscle by IL-1beta and NFkappaB activation: an in vitro and in vivo study." Cardiovasc Res 54(1): 95-104.

Allen, D. L., D. H. Teitelbaum, et al. (2003). "Growth factor stimulation of matrix metalloproteinase expression and myoblast migration and invasion in vitro." Am J Physiol Cell Physiol 284(4): C805-15.

Austin, L., J. Bower, et al. (1992). "Effects of leukaemia inhibitory factor and other cytokines on murine and human myoblast proliferation." J Neurol Sci 112(1-2): 185-91.

Belles-Isles, M., R. Roy, et al. (1993). "Rapid selection of donor myoblast clones for muscular dystrophy therapy using cell surface expression of NCAM." Eur J Histochem 37(4): 375-80.

Bogdanovich, S., K. J. Perkins, et al. (2004). "Therapeutics for Duchenne muscular dystrophy: current approaches and future directions." J Mol Med 82(2): 102-15.

Brewer, G. J., J. R. Torricelli, et al. (1993). "Optimized survival of hippocampal neurons in B27-supplemented Neurobasal, a new serum-free medium combination." J Neurosci Res 35(5): 567-76.

Broussard, S. R., R. H. McCusker, et al. (2004). "IL-1beta impairs insulin-like growth factor i-induced differentiation and downstream activation signals of the insulin-like growth factor i receptor in myoblasts." J Immunol 172(12): 7713-20.

Butler, M. (1991). Mammalian cell biotechnology, a practical approach, Oxford University Press.

Cantini, M., E. Giurisato, et al. (2002). "Macrophage-secreted myogenic factors: a promising tool for greatly enhancing the proliferative capacity of myoblasts in vitro and in vivo." Neurol Sci 23(4): 189-94.

Cantini, M., M. L. Massimino, et al. (1994). "Macrophages regulate proliferation and differentiation of satellite cells." Biochem Biophys Res Commun 202(3): 1688-96.

Caroleo, M. C., N. Costa, et al. (2001). "Human monocyte/macrophages activate by exposure to LPS overexpress NGF and NGF receptors." J Neuroimmunol 113(2): 193-201.

Carpenter, S., G. Karpati, et al. (1990). "Dystrophin is localized to the plasma membrane of human skeletal muscle fibers by electron-microscopic cytochemical study." Muscle Nerve 13(5): 376-80.

Charge, S. B. and M. A. Rudnicki (2004). "Cellular and molecular regulation of muscle regeneration." Physiol Rev 84(1): 209-38.

Chazaud, B., C. Sonnet, et al. (2003). "Satellite cells attract monocytes and use macrophages as a support to escape apoptosis and enhance muscle growth." J Cell Biol 163(5): 1133-43.

Chen, M., H. J. Li, et al. (1992). "Dystrophin cytochemistry in mdx mouse muscles injected with labeled normal myoblasts." Cell Transplant 1(1): 17-22.

Chen, X., Z. Mao, et al. (2005). "Dedifferentiation of adult human myoblasts induced by ciliary neurotrophic factor in vitro." Mol Biol Cell 16(7): 3140-51.

Chevrel, G., C. Granet, et al. (2005). "Contribution of tumour necrosis factor alpha and interleukin (IL) 1beta to IL6 production, NF-kappaB nuclear translocation, and class I MHC expression in muscle cells: in vitro regulation with specific cytokine inhibitors." Ann Rheum Dis 64(9): 1257-62.

Cooper, G. and R. Hausman (2007). The cell a molecular approach, Sinauer Associates, Inc. (a completer)

Davis, J. M. (2002). Basic cell culture: a practical approach, Oxford University Press, 408 pages.

Emery, A., Muntoni, F. (2003). Duchenne muscular dystrophy, Oxford University Press, 282 pages.

Ferrara, N., H. P. Gerber, et al. (2003). "The biology of VEGF and its receptors." Nat Med 9(6): 669-76.

Fitzgerald, K. A., L. A. J. O'Neill, et al. (2001). The cytokine FactsBook. Dundee, Scotland, Academic Press.

Floss, T., H. H. Arnold, et al. (1997). "A role for FGF-6 in skeletal muscle regeneration." Genes Dev 11(16): 2040-51.

Freshney, R. I. (2000). Culture of Animal Cell: A Manual of Basic Technique. New York, Wiley-Liss.

Freshney, R. I. (2005). Culture of animal cells, a manual of basic technique, Wiley-Liss.

Girgenrath, M., S. Weng, et al. (2006). "TWEAK, via its receptor Fn14, is a novel regulator of mesenchymal progenitor cells and skeletal muscle regeneration." Embo J 25(24): 5826-39.

Goto, S., K. Miyazaki, et al. (1999). "Serum-free culture conditions for analysis of secretory proteinases during myogenic differentiation of mouse C2C12 myoblasts." Anal Biochem 272(2): 135-42.

Gussoni, E., G. K. Pavlath, et al. (1992). "Normal dystrophin transcripts detected in Duchenne muscular dystrophy patients after myoblast transplantation." Nature 356(6368): 435-8.

Ham, R. G. and W. L. McKeehan (1979). "Media and growth requirements." Methods Enzymol 58: 44-93.

Ham, R. G., J. A. St Clair, et al. (1988). "Improved media for normal human muscle satellite cells: serum-free clonal growth and enhanced growth with low serum." In Vitro Cell Dev Biol 24(8): 833-44.

Hancock, J. (2005). "Cell signalling." Oxford University Press: 296. (a completer)

Huard, J., J. P. Bouchard, et al. (1992). "Human myoblast transplantation: preliminary results of 4 cases." Muscle Nerve 15(5): 550-60.

Huard, J., S. Verreault, et al. (1994). "High efficiency of muscle regeneration after human myoblast clone transplantation in SCID mice." J Clin Invest 93(2): 586-99.

Jayme, D. W., D. A. Epstein, et al. (1988). "Fetal bovine serum alternatives." Nature 334(6182): 547-8.

John B. Kurek, J. J. B., Jason D. White, Catriona M. Muldoon and and L. Austin (1998). "Leukaemia Inhibitory Factor and Other Cytokines as Factors Influencing Regeneration of Skeletal Muscle." Basic Appl. Myol. 8((5)): 347-360.

Kahn, J. (2006). "Myoblast cell therapy shows promise, but safety issues linger." J Intery Cardiol 19(4): 302-3.

Kinoshita, I., J. T. Vilquin, et al. (1995). "Pretreatment of myoblast cultures with basic fibroblast growth factor increases the efficacy of their transplantation in mdx mice." Muscle Nerve 18(8): 834-41.

Lafreniere, J. F., P. Mills, et al. (2004). "Growth factors improve the in vivo migration of human skeletal myoblasts by modulating their endogenous proteolytic activity." Transplantation 77(11): 1741-7.

Langen, R. C., J. L. Van Der Velden, et al. (2004). "Tumor necrosis factor-alpha inhibits myogenic differentiation through MyoD protein destabilization." Faseb J 18(2): 227-37.

Lewin, B., L. Cassimeris, et al. (2007). Cells, Jones and Bartlett.

Li, Y. P. (2003). "TNF-alpha is a mitogen in skeletal muscle." Am J Physiol Cell Physiol 285(2): C370-6.

Massimino, M. L., E. Rapizzi, et al. (1997). "ED2+ macrophages increase selectively myoblast proliferation in muscle cultures." Biochem Biophys Res Commun 235(3): 754-9.

Mather, J. P., Barnes, D. (1998). Animal cell culture methods, Volume 57, Elsevier science and technology, 368 pages.

Miller, K. J., D. Thaloor, et al. (2000). "Hepatocyte growth factor affects satellite cell activation and differentiation in regenerating skeletal muscle." Am J Physiol Cell Physiol 278(1): C174-81.

Mizel, S. B. (1989). "The interleukins." Faseb J 3(12): 2379-88.

Muntoni, F., S. Brown, et al. (2002). "Muscle development genes: their relevance in neuromuscular disorders." Neuromuscul Disord 12(5): 438-46.

Naomoto, Y., T. Yamatsuji, et al. (2005). "Rational role of amino acids in intestinal epithelial cells (Review)." Int J Mol Med 16(2): 201-4.

Nomura, T., E. Ashihara, et al. (2007). "Therapeutic potential of stem/progenitor cells in human skeletal muscle for cardiovascular regeneration." Curr Stem Cell Res Ther 2(4): 293-300.

Omenn, G. S., D. J. States, et al. (2005). "Overview of the HUPO Plasma Proteome Project: results from the pilot phase with 35 collaborating laboratories and multiple analytical groups, generating a core dataset of 3020 proteins and a publicly-available database." Proteomics 5(13): 3226-45.

Schlessinger, J. and A. Ullrich (1992). "Growth factor signaling by receptor tyrosine kinases." Neuron 9(3): 383-91.

Skuk, D., M. Goulet, et al. (2006). "Dystrophin expression in muscles of duchenne muscular dystrophy patients after high-density injections of normal myogenic cells." J Neuropathol Exp Neurol 65(4): 371-86.

Skuk, D., M. Goulet, et al. (2007). "First test of a "high-density injection" protocol for myogenic cell transplantation throughout large volumes of muscles in a Duchenne muscular dystrophy patient: eighteen months follow-up." Neuromuscul Disord 17(1): 38-46.

Skuk, D. and J. P. Tremblay (2000). "Progress in myoblast transplantation: a potential treatment of dystrophies." Microsc Res Tech 48(3-4): 213-22.

Skuk, D., J. T. Vilquin, et al. (2002). "Experimental and therapeutic approaches to muscular dystrophies." Curr Opin Neurol 15(5): 563-9.

Strle, K., S. R. Broussard, et al. (2004). "Proinflammatory cytokine impairment of insulin-like growth factor I-induced protein synthesis in skeletal muscle myoblasts requires ceramide." Endocrinology 145(10): 4592-602.

Tidball, J. G. (2005). "Inflammatory processes in muscle injury and repair." Am J Physiol Regul lntegr Comp Physiol 288(2): R345-53.

Torrente, Y., E. El Fahime, et al. (2003). "Tumor necrosis factor-alpha (TNF-alpha) stimulates chemotactic response in mouse myogenic cells." Cell Transplant 12(1): 91-100.

Totsuka, T. (1987), "Centronucleated Myofibers Having Also Peripheral Nuclei in Rectus Femoris Muscles of Muscular Dystrophic Mice". Cong Anom 27: 51-60.

Voisin, V. and S. de la Porte (2004). "Therapeutic strategies for Duchenne and Becker dystrophies." Int Rev Cytol 240: 1-30.

Whang, X., Z. Bi et al. (2005). "IL-1 receptor antagonist attenuates MAP kinase/AP-1 activation and MMPI expression in UVA-irradiated human fibroblasts induced by culture medium from UVB-irradiated human skin keratinocytes". Int J Mol Med 16(6):1117-24.

White, J. D., M. Davies, et al. (2001). "Leukaemia inhibitory factor increases myoblast replication and survival and affects extracellular matrix production: combined in vivo and in vitro studies in post-natal skeletal muscle." Cell Tissue Res 306(1): 129-41.

Yiou, R., L. Zini, et al. (2004). "Thérapie cellulaire de l'insuffisance sphinctérienne urétrale par autogreffe de cellules précurseur musculaire." Progrès en Urologie(14): 93-99.

Zimmerman, A. M., J. L. Vierck, et al. (2000). "Formulation of a defined medium to maintain cell health and viability in vitro." Methods Cell Sci 22(1): 43-9.

What is claimed is:

1. A culture medium for a cell of a myogenic lineage, said culture medium comprising:
   a basal medium;
   a growth factor that is at least one of a fibroblast growth factor (FGF), an epidermal growth factor (EGF) and an insulin-like growth factor (IGF), wherein the growth factor has a concentration in the culture medium that is between about 1 ng/mL and about 100 ng/mL; and
   an interleukin that is at least one of IL-1, IL-6, IL-8, IL-18 and IL-33, wherein the interleukin has a concentration in the culture medium that is between about 0.1 ng/mL and about 100 ng/mL;
   wherein the culture medium is free of serum and allows proliferation of the cell of the myogenic lineage at a similar rate of proliferation to the rate of proliferation of another cell of the myogenic lineage that is cultured in a standard medium containing serum.

2. The culture medium of claim 1, wherein the cell of the myogenic lineage is at least one of a muscular stem cell, a myoblast and a myoblast-derived cell.

3. The culture medium of claim 1, wherein the basal medium is at least one of Dulbecco's modified Eagles's medium (DMEM), advanced DMEM, Ham's F10, Ham's F12, Iscove's modified Dulbecco's medium, neurobasal medium, RPMI 1640 and MCDB120 medium.

4. The culture medium of claim 1, further comprising a supplement.

5. The culture medium of claim 4, wherein the supplement is at least one of:
   a combination of insulin, transferrin and selenite (ITS);
   B27™;
   a combination of dexamethasone, insulin, EGF, fetuin and albumin; and
   a combination of dexamethasone, bFGF, albumin and insulin.

6. The culture medium of claim 1, further comprising a lipid.

7. The culture medium of claim 6, wherein the lipid is at least one of arachidonic acid, cholesterol, DL-α-tocopherol acetate, linoleic acid, linolenic acid, myristic acid, oleic acid, palmitoleic acid, palmitic acid and stearic acid.

8. The culture medium of claim 1, wherein the growth factor is a combination of FGF, EGF and IGF.

9. The culture medium of claim 8, wherein FGF is a combination of bFGF and FGF4.

10. The culture medium of claim 8, wherein IGF is IGF-1.

11. The culture medium of claim 1, wherein the interleukin is IL-1.

12. The culture medium of claim 11, wherein the IL-1 is a combination of IL-1α and IL-1β.

13. An in vitro method of culturing a cell of a myogenic lineage, said method comprising contacting the cell of the myogenic lineage with the culture medium of claim 1, thereby culturing said cell.

14. The in vitro method of claim 13, wherein the cell of the myogenic lineage is at least one of a muscular stem cell, a myoblast and a myoblast-derived cell.

15. The in vitro method of claim 14, wherein the myoblast-derived cell is at least one of a muscle cell, a satellite cell and a myocyte.

16. The in vitro method of claim 13, wherein the method is performed for at least an hour.

17. The in vitro method of claim 13, wherein the method is performed for at least a day.

18. The in vitro method of claim 13, wherein the method is performed for at least a week.

19. The in vitro method of claim 13, wherein said method reduces a lag phase of the cell of the myogenic lineage that is cultured in said culture medium of claim 1, with respect to the lag phase of a cell of the myogenic lineage that is cultured in another serum-free media.

20. The in vitro method of claim 13, wherein said method enables long term expansion of the cell of the myogenic lineage.

21. The in vitro method of claim 13, wherein an initial concentration of the cell of the myogenic lineage in the culture medium is 10,000 cells/mL.

22. The in vitro method of claim 13, wherein the method enables the cell of the myogenic lineage to retain its ability to form a myotube.

* * * * *

```
SEQUENCE LISTING

<160> NUMBER OF SEQ ID NOS: 188

<210> SEQ ID NO 1
<211> LENGTH: 17
<212> TYPE: DNA
<213> ORGANISM: Artificial Sequence
<220> FEATURE:
<223> OTHER INFORMATION: Oligonucleotide

<400> SEQUENCE: 1
agcctcgcct ttgccga                                                          17

<210> SEQ ID NO 2
<211> LENGTH: 15
<212> TYPE: DNA
<213> ORGANISM: Artificial Sequence
<220> FEATURE:
<223> OTHER INFORMATION: Oligonucleotide

<400> SEQUENCE: 2
ctggtgcctg gggcg                                                            15

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide

<400> SEQUENCE: 3
tactgctgca gatggacctg                                                       20

<210> SEQ ID NO 4
<211> LENGTH: 19
<212> TYPE: DNA
<213> ORGANISM: Artificial Sequence
<220> FEATURE:
<223> OTHER INFORMATION: Oligonucleotide

<400> SEQUENCE: 4
agctccagtt cagagtccc                                                        19

<210> SEQ ID NO 5
<211> LENGTH: 19
<212> TYPE: DNA
<213> ORGANISM: Artificial Sequence
<220> FEATURE:
<223> OTHER INFORMATION: Oligonucleotide

<400> SEQUENCE: 5
gcaattgctc atcgagacc                                                        19
```

```
<210> SEQ ID NO 6
<211> LENGTH: 20
<212> TYPE: DNA
<213> ORGANISM: Artificial Sequence
<220> FEATURE:
<223> OTHER INFORMATION: Oligonucleotide

<400> SEQUENCE: 6
cgaaggtgta gatgtcagcc                                                   20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide

<400> SEQUENCE: 7
gcagcacaga cggatattgt                                                   20

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide

<400> SEQUENCE: 8
tttcatgcct catcaacact                                                   20

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide

<400> SEQUENCE: 9
acgggagaga agacgagcct                                                   20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide

<400> SEQUENCE: 10
ctagatcaag agagggttcg                                                   20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide

<400> SEQUENCE: 11
ggtcaattca gcgaagtcct                                                   20

<210> SEQ ID NO 12
<211> LENGTH: 21
<212> TYPE: DNA
<213> ORGANISM: Artificial Sequence
<220> FEATURE:
```

```
<223> OTHER INFORMATION: Oligonucleotide

<400> SEQUENCE: 12
ttcgtgatct tcttcccagt g                                              21

<210> SEQ ID NO 13
<211> LENGTH: 24
<212> TYPE: DNA
<213> ORGANISM: Artificial Sequence
<220> FEATURE:
<223> OTHER INFORMATION: Oligonucleotide

<400> SEQUENCE: 13
ggaaacagac aagcaaccca aact                                           24

<210> SEQ ID NO 14
<211> LENGTH: 26
<212> TYPE: DNA
<213> ORGANISM: Artificial Sequence
<220> FEATURE:
<223> OTHER INFORMATION: Oligonucleotide

<400> SEQUENCE: 14
ggtcatgttc ggttggtcaa agataa                                         26

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide

<400> SEQUENCE: 15
tctgaagctg aggagtggta                                                20

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide

<400> SEQUENCE: 16
cttcttggta tggacctcag                                                20

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide

<400> SEQUENCE: 17
gttgtaagga gcgggtgaac                                                20

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide

<400> SEQUENCE: 18
gccagcaacc catacttgtt                                                20
```

```
<210> SEQ ID NO 19
<211> LENGTH: 20
<212> TYPE: DNA
<213> ORGANISM: Artificial Sequence
<220> FEATURE:
<223> OTHER INFORMATION: Oligonucleotide

<400> SEQUENCE: 19
ggtcaatgca accaacttca                                                  20

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide

<400> SEQUENCE: 20
ggcattgagt aggtgattag                                                  20

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide

<400> SEQUENCE: 21
atgtccggga acacaaagac                                                  20

<210> SEQ ID NO 22
<211> LENGTH: 20
<212> TYPE: DNA
<213> ORGANISM: Artificial Sequence
<220> FEATURE:
<223> OTHER INFORMATION: Oligonucleotide

<400> SEQUENCE: 22
ttccgtcata tggcttggat                                                  20

<210> SEQ ID NO 23
<211> LENGTH: 22
<212> TYPE: DNA
<213> ORGANISM: Artificial Sequence
<220> FEATURE:
<223> OTHER INFORMATION: Oligonucleotide

<400> SEQUENCE: 23
gataaagccg tcagtggcct tc                                               22

<210> SEQ ID NO 24
<211> LENGTH: 21
<212> TYPE: DNA
<213> ORGANISM: Artificial Sequence
<220> FEATURE:
<223> OTHER INFORMATION: Oligonucleotide

<400> SEQUENCE: 24
gggagatggc ttccttctgg g                                                21

<210> SEQ ID NO 25
<211> LENGTH: 20
<212> TYPE: DNA
<213> ORGANISM: Artificial Sequence
<220> FEATURE:
<223> OTHER INFORMATION: Oligonucleotide
```

```
<400> SEQUENCE: 25
cctgacgctc tccctcatcc                                              20

<210> SEQ ID NO 26
<211> LENGTH: 21
<212> TYPE: DNA
<213> ORGANISM: Artificial Sequence
<220> FEATURE:
<223> OTHER INFORMATION: Oligonucleotide

<400> SEQUENCE: 26
gccttcaaac tcgctctctg g                                            21

<210> SEQ ID NO 27
<211> LENGTH: 21
<212> TYPE: DNA
<213> ORGANISM: Artificial Sequence
<220> FEATURE:
<223> OTHER INFORMATION: Oligonucleotide

<400> SEQUENCE: 27
catggctgaa ggggaaatca c                                            21

<210> SEQ ID NO 28
<211> LENGTH: 22
<212> TYPE: DNA
<213> ORGANISM: Artificial Sequence
<220> FEATURE:
<223> OTHER INFORMATION: Oligonucleotide

<400> SEQUENCE: 28
aatcagaaga gactggcagg gg                                           22

<210> SEQ ID NO 29
<211> LENGTH: 21
<212> TYPE: DNA
<213> ORGANISM: Artificial Sequence
<220> FEATURE:
<223> OTHER INFORMATION: Oligonucleotide

<400> SEQUENCE: 29
tcaccacgct gcccgccttg c                                            21

<210> SEQ ID NO 30
<211> LENGTH: 21
<212> TYPE: DNA
<213> ORGANISM: Artificial Sequence
<220> FEATURE:
<223> OTHER INFORMATION: Oligonucleotide

<400> SEQUENCE: 30
cagttcgttt cagtgccaca t                                            21

<210> SEQ ID NO 31
<211> LENGTH: 20
<212> TYPE: DNA
<213> ORGANISM: Artificial Sequence
<220> FEATURE:
<223> OTHER INFORMATION: Oligonucleotide

<400> SEQUENCE: 31
ttggagataa cggcagtgga                                              20

<210> SEQ ID NO 32
<211> LENGTH: 20
```

<210> SEQ ID NO 32
<211> LENGTH: 20
<212> TYPE: DNA
<213> ORGANISM: Artificial Sequence
<220> FEATURE:
<223> OTHER INFORMATION: Oligonucleotide

<400> SEQUENCE: 32
ctccaggtta tccgggctct                                               20

<210> SEQ ID NO 33
<211> LENGTH: 27
<212> TYPE: DNA
<213> ORGANISM: Artificial Sequence
<220> FEATURE:
<223> OTHER INFORMATION: Oligonucleotide

<400> SEQUENCE: 33
gctgtgtctc aggggattgt aggaata                                       27

<210> SEQ ID NO 34
<211> LENGTH: 26
<212> TYPE: DNA
<213> ORGANISM: Artificial Sequence
<220> FEATURE:
<223> OTHER INFORMATION: Oligonucleotide

<400> SEQUENCE: 34
tatccaaagc gaaacttgag tctgta                                        26

<210> SEQ ID NO 35
<211> LENGTH: 24
<212> TYPE: DNA
<213> ORGANISM: Artificial Sequence
<220> FEATURE:
<223> OTHER INFORMATION: Oligonucleotide

<400> SEQUENCE: 35
acccggagca ctacactata atgc                                          24

<210> SEQ ID NO 36
<211> LENGTH: 24
<212> TYPE: DNA
<213> ORGANISM: Artificial Sequence
<220> FEATURE:
<223> OTHER INFORMATION: Oligonucleotide

<400> SEQUENCE: 36
ttattgccat aggaagaaag tggg                                          24

<210> SEQ ID NO 37
<211> LENGTH: 20
<212> TYPE: DNA
<213> ORGANISM: Artificial Sequence
<220> FEATURE:
<223> OTHER INFORMATION: Oligonucleotide

<400> SEQUENCE: 37
gagatgtccg ctggagaaag                                               20

<210> SEQ ID NO 38
<211> LENGTH: 20
<212> TYPE: DNA
<213> ORGANISM: Artificial Sequence
<220> FEATURE:
<223> OTHER INFORMATION: Oligonucleotide

<400> SEQUENCE: 38

-continued atttgcctcc cattatgctg                                                                20

<210> SEQ ID NO 39
<211> LENGTH: 19
<212> TYPE: DNA
<213> ORGANISM: Artificial Sequence
<220> FEATURE:
<223> OTHER INFORMATION: Oligonucleotide

<400> SEQUENCE: 39
aaggtccgtt atgccacct                                                                 19

<210> SEQ ID NO 40
<211> LENGTH: 19
<212> TYPE: DNA
<213> ORGANISM: Artificial Sequence
<220> FEATURE:
<223> OTHER INFORMATION: Oligonucleotide

<400> SEQUENCE: 40
caggttgtct gggccaatc                                                                 19

<210> SEQ ID NO 41
<211> LENGTH: 20
<212> TYPE: DNA
<213> ORGANISM: Artificial Sequence
<220> FEATURE:
<223> OTHER INFORMATION: Oligonucleotide

<400> SEQUENCE: 41
ggaaaagaac ggcagtaaat                                                                20

<210> SEQ ID NO 42
<211> LENGTH: 20
<212> TYPE: DNA
<213> ORGANISM: Artificial Sequence
<220> FEATURE:
<223> OTHER INFORMATION: Oligonucleotide

<400> SEQUENCE: 42
gtagtctggg gaagctgtaa                                                                20

<210> SEQ ID NO 43
<211> LENGTH: 19
<212> TYPE: DNA
<213> ORGANISM: Artificial Sequence
<220> FEATURE:
<223> OTHER INFORMATION: Oligonucleotide

<400> SEQUENCE: 43
gggcccctta ctggacacg                                                                 19

<210> SEQ ID NO 44
<211> LENGTH: 18
<212> TYPE: DNA
<213> ORGANISM: Artificial Sequence
<220> FEATURE:
<223> OTHER INFORMATION: Oligonucleotide

<400> SEQUENCE: 44
gccggatgct gccaaact                                                                  18

<210> SEQ ID NO 45
<211> LENGTH: 18
<212> TYPE: DNA
<213> ORGANISM: Artificial Sequence

```
<220> FEATURE:
<223> OTHER INFORMATION: Oligonucleotide

<400> SEQUENCE: 45
cgctggctta aggatgga                                                 18

<210> SEQ ID NO 46
<211> LENGTH: 18
<212> TYPE: DNA
<213> ORGANISM: Artificial Sequence
<220> FEATURE:
<223> OTHER INFORMATION: Oligonucleotide

<400> SEQUENCE: 46
ctgcccacag cgttctct                                                 18

<210> SEQ ID NO 47
<211> LENGTH: 19
<212> TYPE: DNA
<213> ORGANISM: Artificial Sequence
<220> FEATURE:
<223> OTHER INFORMATION: Oligonucleotide

<400> SEQUENCE: 47
acctgagcgt catgtaccg                                                19

<210> SEQ ID NO 48
<211> LENGTH: 20
<212> TYPE: DNA
<213> ORGANISM: Artificial Sequence
<220> FEATURE:
<223> OTHER INFORMATION: Oligonucleotide

<400> SEQUENCE: 48
tgtggcacga ggagatgtag                                               20

<210> SEQ ID NO 49
<211> LENGTH: 21
<212> TYPE: DNA
<213> ORGANISM: Artificial Sequence
<220> FEATURE:
<223> OTHER INFORMATION: Oligonucleotide

<400> SEQUENCE: 49
gccaaggtca tccatgacaa c                                             21

<210> SEQ ID NO 50
<211> LENGTH: 21
<212> TYPE: DNA
<213> ORGANISM: Artificial Sequence
<220> FEATURE:
<223> OTHER INFORMATION: Oligonucleotide

<400> SEQUENCE: 50
gtccaccacc ctgttgctgt a                                             21

<210> SEQ ID NO 51
<211> LENGTH: 24
<212> TYPE: DNA
<213> ORGANISM: Artificial Sequence
<220> FEATURE:
<223> OTHER INFORMATION: Oligonucleotide

<400> SEQUENCE: 51
agcttcctgc tcaagtgctt agag                                          24
```

<210> SEQ ID NO 52
<211> LENGTH: 24
<212> TYPE: DNA
<213> ORGANISM: Artificial Sequence
<220> FEATURE:
<223> OTHER INFORMATION: Oligonucleotide

<400> SEQUENCE: 52
ttcttccatc tgctgccaga tggt                                          24

<210> SEQ ID NO 53
<211> LENGTH: 24
<212> TYPE: DNA
<213> ORGANISM: Artificial Sequence
<220> FEATURE:
<223> OTHER INFORMATION: Oligonucleotide

<400> SEQUENCE: 53
gtctcctgaa cctgagtaga gaca                                          24

<210> SEQ ID NO 54
<211> LENGTH: 24
<212> TYPE: DNA
<213> ORGANISM: Artificial Sequence
<220> FEATURE:
<223> OTHER INFORMATION: Oligonucleotide

<400> SEQUENCE: 54
aaggggatga caagcagaaa gtcc                                          24

<210> SEQ ID NO 55
<211> LENGTH: 17
<212> TYPE: DNA
<213> ORGANISM: Artificial Sequence
<220> FEATURE:
<223> OTHER INFORMATION: Oligonucleotide

<400> SEQUENCE: 55
cttctctctg accagca                                                  17

<210> SEQ ID NO 56
<211> LENGTH: 17
<212> TYPE: DNA
<213> ORGANISM: Artificial Sequence
<220> FEATURE:
<223> OTHER INFORMATION: Oligonucleotide

<400> SEQUENCE: 56
acatgggttc ctgagtc                                                  17

<210> SEQ ID NO 57
<211> LENGTH: 20
<212> TYPE: DNA
<213> ORGANISM: Artificial Sequence
<220> FEATURE:
<223> OTHER INFORMATION: Oligonucleotide

<400> SEQUENCE: 57
tggagtggcc tctggttatg                                               20

<210> SEQ ID NO 58
<211> LENGTH: 22
<212> TYPE: DNA
<213> ORGANISM: Artificial Sequence
<220> FEATURE:
<223> OTHER INFORMATION: Oligonucleotide

```
<400> SEQUENCE: 58
gggaactagg gagacagacg ag                                          22

<210> SEQ ID NO 59
<211> LENGTH: 24
<212> TYPE: DNA
<213> ORGANISM: Artificial Sequence
<220> FEATURE:
<223> OTHER INFORMATION: Oligonucleotide

<400> SEQUENCE: 59
ggtgctgaag ctctttctgg ctgc                                        24

<210> SEQ ID NO 60
<211> LENGTH: 24
<212> TYPE: DNA
<213> ORGANISM: Artificial Sequence
<220> FEATURE:
<223> OTHER INFORMATION: Oligonucleotide

<400> SEQUENCE: 60
attatgggag gcccaatcct agac                                        24

<210> SEQ ID NO 61
<211> LENGTH: 22
<212> TYPE: DNA
<213> ORGANISM: Artificial Sequence
<220> FEATURE:
<223> OTHER INFORMATION: Oligonucleotide

<400> SEQUENCE: 61
ctacactgga ttgatcaact at                                          22

<210> SEQ ID NO 62
<211> LENGTH: 22
<212> TYPE: DNA
<213> ORGANISM: Artificial Sequence
<220> FEATURE:
<223> OTHER INFORMATION: Oligonucleotide

<400> SEQUENCE: 62
agtagttgtc ttaggattgt tg                                          22

<210> SEQ ID NO 63
<211> LENGTH: 20
<212> TYPE: DNA
<213> ORGANISM: Artificial Sequence
<220> FEATURE:
<223> OTHER INFORMATION: Oligonucleotide

<400> SEQUENCE: 63
aaatcagcag tcttccaacc                                             20

<210> SEQ ID NO 64
<211> LENGTH: 20
<212> TYPE: DNA
<213> ORGANISM: Artificial Sequence
<220> FEATURE:
<223> OTHER INFORMATION: Oligonucleotide

<400> SEQUENCE: 64
cttctgggtc ttgggcatgt                                             20

<210> SEQ ID NO 65
```

<211> LENGTH: 20
<212> TYPE: DNA
<213> ORGANISM: Artificial Sequence
<220> FEATURE:
<223> OTHER INFORMATION: Oligonucleotide

<400> SEQUENCE: 65
ctgctgatgt gtacgttcct                                        20

<210> SEQ ID NO 66
<211> LENGTH: 19
<212> TYPE: DNA
<213> ORGANISM: Artificial Sequence
<220> FEATURE:
<223> OTHER INFORMATION: Oligonucleotide

<400> SEQUENCE: 66
caggttcatc tttcaccac                                         19

<210> SEQ ID NO 67
<211> LENGTH: 20
<212> TYPE: DNA
<213> ORGANISM: Artificial Sequence
<220> FEATURE:
<223> OTHER INFORMATION: Oligonucleotide

<400> SEQUENCE: 67
cctggagacg tactgtgcta                                        20

<210> SEQ ID NO 68
<211> LENGTH: 18
<212> TYPE: DNA
<213> ORGANISM: Artificial Sequence
<220> FEATURE:
<223> OTHER INFORMATION: Oligonucleotide

<400> SEQUENCE: 68
ggactgcttc caggtgtc                                          18

<210> SEQ ID NO 69
<211> LENGTH: 20
<212> TYPE: DNA
<213> ORGANISM: Artificial Sequence
<220> FEATURE:
<223> OTHER INFORMATION: Oligonucleotide

<400> SEQUENCE: 69
gctgtttgta tgcacgactt                                        20

<210> SEQ ID NO 70
<211> LENGTH: 20
<212> TYPE: DNA
<213> ORGANISM: Artificial Sequence
<220> FEATURE:
<223> OTHER INFORMATION: Oligonucleotide

<400> SEQUENCE: 70
tgctctggac tctgtgattt                                        20

<210> SEQ ID NO 71
<211> LENGTH: 19
<212> TYPE: DNA
<213> ORGANISM: Artificial Sequence
<220> FEATURE:
<223> OTHER INFORMATION: Oligonucleotide

<400> SEQUENCE: 71

-continued

```
ctacgccccg ctcacaaag                                                19

<210> SEQ ID NO 72
<211> LENGTH: 20
<212> TYPE: DNA
<213> ORGANISM: Artificial Sequence
<220> FEATURE:
<223> OTHER INFORMATION: Oligonucleotide

<400> SEQUENCE: 72
ggcagaggag atggcaggag                                               20

<210> SEQ ID NO 73
<211> LENGTH: 26
<212> TYPE: DNA
<213> ORGANISM: Artificial Sequence
<220> FEATURE:
<223> OTHER INFORMATION: Oligonucleotide

<400> SEQUENCE: 73
gtctctgaat cagaaatcct tctatc                                        26

<210> SEQ ID NO 74
<211> LENGTH: 25
<212> TYPE: DNA
<213> ORGANISM: Artificial Sequence
<220> FEATURE:
<223> OTHER INFORMATION: Oligonucleotide

<400> SEQUENCE: 74
catgtcaaat ttcactgctt catcc                                         25

<210> SEQ ID NO 75
<211> LENGTH: 20
<212> TYPE: DNA
<213> ORGANISM: Artificial Sequence
<220> FEATURE:
<223> OTHER INFORMATION: Oligonucleotide

<400> SEQUENCE: 75
tgaactgaaa gctctccacc                                               20

<210> SEQ ID NO 76
<211> LENGTH: 20
<212> TYPE: DNA
<213> ORGANISM: Artificial Sequence
<220> FEATURE:
<223> OTHER INFORMATION: Oligonucleotide

<400> SEQUENCE: 76
ctgatgtacc agttggggaa                                               20

<210> SEQ ID NO 77
<211> LENGTH: 22
<212> TYPE: DNA
<213> ORGANISM: Artificial Sequence
<220> FEATURE:
<223> OTHER INFORMATION: Oligonucleotide

<400> SEQUENCE: 77
ggaagccgtg gttatctctg tt                                            22

<210> SEQ ID NO 78
<211> LENGTH: 22
<212> TYPE: DNA
```

```
<213> ORGANISM: Artificial Sequence
<220> FEATURE:
<223> OTHER INFORMATION: Oligonucleotide

<400> SEQUENCE: 78
ggtgggttga atgaaggaaa gt                                              22

<210> SEQ ID NO 79
<211> LENGTH: 23
<212> TYPE: DNA
<213> ORGANISM: Artificial Sequence
<220> FEATURE:
<223> OTHER INFORMATION: Oligonucleotide

<400> SEQUENCE: 79
atcccacacg ccacattcaa agc                                             23

<210> SEQ ID NO 80
<211> LENGTH: 23
<212> TYPE: DNA
<213> ORGANISM: Artificial Sequence
<220> FEATURE:
<223> OTHER INFORMATION: Oligonucleotide

<400> SEQUENCE: 80
tgccccacca cgaaatgata aat                                             23

<210> SEQ ID NO 81
<211> LENGTH: 20
<212> TYPE: DNA
<213> ORGANISM: Artificial Sequence
<220> FEATURE:
<223> OTHER INFORMATION: Oligonucleotide

<400> SEQUENCE: 81
gcccccatct ccctccaagt                                                 20

<210> SEQ ID NO 82
<211> LENGTH: 20
<212> TYPE: DNA
<213> ORGANISM: Artificial Sequence
<220> FEATURE:
<223> OTHER INFORMATION: Oligonucleotide

<400> SEQUENCE: 82
aggggaaggg cgaagagagc                                                 20

<210> SEQ ID NO 83
<211> LENGTH: 22
<212> TYPE: DNA
<213> ORGANISM: Artificial Sequence
<220> FEATURE:
<223> OTHER INFORMATION: Oligonucleotide

<400> SEQUENCE: 83
acccaccaat cacgaaccta ag                                              22

<210> SEQ ID NO 84
<211> LENGTH: 23
<212> TYPE: DNA
<213> ORGANISM: Artificial Sequence
<220> FEATURE:
<223> OTHER INFORMATION: Oligonucleotide

<400> SEQUENCE: 84
ggtcacattt ctgttaaggt ccc                                             23
```

<210> SEQ ID NO 85
<211> LENGTH: 25
<212> TYPE: DNA
<213> ORGANISM: Artificial Sequence
<220> FEATURE:
<223> OTHER INFORMATION: Oligonucleotide

<400> SEQUENCE: 85
actctgtgca ccgagttgac cgtaa                                              25

<210> SEQ ID NO 86
<211> LENGTH: 25
<212> TYPE: DNA
<213> ORGANISM: Artificial Sequence
<220> FEATURE:
<223> OTHER INFORMATION: Oligonucleotide

<400> SEQUENCE: 86
tctcatgatc gtctttagcc tttcc                                              25

<210> SEQ ID NO 87
<211> LENGTH: 20
<212> TYPE: DNA
<213> ORGANISM: Artificial Sequence
<220> FEATURE:
<223> OTHER INFORMATION: Oligonucleotide

<400> SEQUENCE: 87
tgcgtctccg actacatgag                                                    20

<210> SEQ ID NO 88
<211> LENGTH: 19
<212> TYPE: DNA
<213> ORGANISM: Artificial Sequence
<220> FEATURE:
<223> OTHER INFORMATION: Oligonucleotide

<400> SEQUENCE: 88
tgactgcata ggtgagatg                                                     19

<210> SEQ ID NO 89
<211> LENGTH: 21
<212> TYPE: DNA
<213> ORGANISM: Artificial Sequence
<220> FEATURE:
<223> OTHER INFORMATION: Oligonucleotide

<400> SEQUENCE: 89
tgcctacgtg tatgccatcc c                                                  21

<210> SEQ ID NO 90
<211> LENGTH: 21
<212> TYPE: DNA
<213> ORGANISM: Artificial Sequence
<220> FEATURE:
<223> OTHER INFORMATION: Oligonucleotide

<400> SEQUENCE: 90
cttggccctc attctcactg c                                                  21

<210> SEQ ID NO 91
<211> LENGTH: 20
<212> TYPE: DNA
<213> ORGANISM: Artificial Sequence
<220> FEATURE:

```
<223> OTHER INFORMATION: Oligonucleotide

<400> SEQUENCE: 91
ccctgaggac acgcagtatt                                          20

<210> SEQ ID NO 92
<211> LENGTH: 20
<212> TYPE: DNA
<213> ORGANISM: Artificial Sequence
<220> FEATURE:
<223> OTHER INFORMATION: Oligonucleotide

<400> SEQUENCE: 92
tgatcaaagg gcctgatagc                                          20

<210> SEQ ID NO 93
<211> LENGTH: 23
<212> TYPE: DNA
<213> ORGANISM: Artificial Sequence
<220> FEATURE:
<223> OTHER INFORMATION: Oligonucleotide

<400> SEQUENCE: 93
atgaactcct tctccacaag cgc                                      23

<210> SEQ ID NO 94
<211> LENGTH: 22
<212> TYPE: DNA
<213> ORGANISM: Artificial Sequence
<220> FEATURE:
<223> OTHER INFORMATION: Oligonucleotide

<400> SEQUENCE: 94
gaagagccct caggctggac tg                                       22

<210> SEQ ID NO 95
<211> LENGTH: 22
<212> TYPE: DNA
<213> ORGANISM: Artificial Sequence
<220> FEATURE:
<223> OTHER INFORMATION: Oligonucleotide

<400> SEQUENCE: 95
cattgccatt gttctgaggt tc                                       22

<210> SEQ ID NO 96
<211> LENGTH: 22
<212> TYPE: DNA
<213> ORGANISM: Artificial Sequence
<220> FEATURE:
<223> OTHER INFORMATION: Oligonucleotide

<400> SEQUENCE: 96
agtagtctgt attgctgatg tc                                       22

<210> SEQ ID NO 97
<211> LENGTH: 21
<212> TYPE: DNA
<213> ORGANISM: Artificial Sequence
<220> FEATURE:
<223> OTHER INFORMATION: Oligonucleotide

<400> SEQUENCE: 97
tctaatggtc agcatcgatc a                                        21
```

<210> SEQ ID NO 98
<211> LENGTH: 20
<212> TYPE: DNA
<213> ORGANISM: Artificial Sequence
<220> FEATURE:
<223> OTHER INFORMATION: Oligonucleotide

<400> SEQUENCE: 98
gtggagatca aaatcaccag                                               20

<210> SEQ ID NO 99
<211> LENGTH: 20
<212> TYPE: DNA
<213> ORGANISM: Artificial Sequence
<220> FEATURE:
<223> OTHER INFORMATION: Oligonucleotide

<400> SEQUENCE: 99
tgctcaaaat ggagacttgg                                               20

<210> SEQ ID NO 100
<211> LENGTH: 19
<212> TYPE: DNA
<213> ORGANISM: Artificial Sequence
<220> FEATURE:
<223> OTHER INFORMATION: Oligonucleotide

<400> SEQUENCE: 100
gagggcccca catatttca                                                19

<210> SEQ ID NO 101
<211> LENGTH: 20
<212> TYPE: DNA
<213> ORGANISM: Artificial Sequence
<220> FEATURE:
<223> OTHER INFORMATION: Oligonucleotide

<400> SEQUENCE: 101
tgagaaccaa gacccagaca                                               20

<210> SEQ ID NO 102
<211> LENGTH: 20
<212> TYPE: DNA
<213> ORGANISM: Artificial Sequence
<220> FEATURE:
<223> OTHER INFORMATION: Oligonucleotide

<400> SEQUENCE: 102
tcatggcttt gtagatgcct                                               20

<210> SEQ ID NO 103
<211> LENGTH: 21
<212> TYPE: DNA
<213> ORGANISM: Artificial Sequence
<220> FEATURE:
<223> OTHER INFORMATION: Oligonucleotide

<400> SEQUENCE: 103
atgaactgtg tttgccgcct g                                             21

<210> SEQ ID NO 104
<211> LENGTH: 21
<212> TYPE: DNA
<213> ORGANISM: Artificial Sequence
<220> FEATURE:
<223> OTHER INFORMATION: Oligonucleotide

<400> SEQUENCE: 104
gagctgtaga gctcccagtg c             21

<210> SEQ ID NO 105
<211> LENGTH: 20
<212> TYPE: DNA
<213> ORGANISM: Artificial Sequence
<220> FEATURE:
<223> OTHER INFORMATION: Oligonucleotide

<400> SEQUENCE: 105
tcacaaagga ggcgaggttc             20

<210> SEQ ID NO 106
<211> LENGTH: 20
<212> TYPE: DNA
<213> ORGANISM: Artificial Sequence
<220> FEATURE:
<223> OTHER INFORMATION: Oligonucleotide

<400> SEQUENCE: 106
tgaacggcat ccaccatgac             20

<210> SEQ ID NO 107
<211> LENGTH: 20
<212> TYPE: DNA
<213> ORGANISM: Artificial Sequence
<220> FEATURE:
<223> OTHER INFORMATION: Oligonucleotide

<400> SEQUENCE: 107
aaggaatacc agtcccgaca             20

<210> SEQ ID NO 108
<211> LENGTH: 21
<212> TYPE: DNA
<213> ORGANISM: Artificial Sequence
<220> FEATURE:
<223> OTHER INFORMATION: Oligonucleotide

<400> SEQUENCE: 108
accagggaac catgaaacaa g             21

<210> SEQ ID NO 109
<211> LENGTH: 20
<212> TYPE: DNA
<213> ORGANISM: Artificial Sequence
<220> FEATURE:
<223> OTHER INFORMATION: Oligonucleotide

<400> SEQUENCE: 109
gtgaaacatg gaagaccatc             20

<210> SEQ ID NO 110
<211> LENGTH: 24
<212> TYPE: DNA
<213> ORGANISM: Artificial Sequence
<220> FEATURE:
<223> OTHER INFORMATION: Oligonucleotide

<400> SEQUENCE: 110
gtgaaataac tggatctgat aggc             24

<210> SEQ ID NO 111
<211> LENGTH: 21

<212> TYPE: DNA
<213> ORGANISM: Artificial Sequence
<220> FEATURE:
<223> OTHER INFORMATION: Oligonucleotide

<400> SEQUENCE: 111
tcttcatttt gggctgtttc a                                            21

<210> SEQ ID NO 112
<211> LENGTH: 21
<212> TYPE: DNA
<213> ORGANISM: Artificial Sequence
<220> FEATURE:
<223> OTHER INFORMATION: Oligonucleotide

<400> SEQUENCE: 112
gtgaacatca ctttccgtat a                                            21

<210> SEQ ID NO 113
<211> LENGTH: 18
<212> TYPE: DNA
<213> ORGANISM: Artificial Sequence
<220> FEATURE:
<223> OTHER INFORMATION: Oligonucleotide

<400> SEQUENCE: 113
cgccaggtgt gtatccac                                                18

<210> SEQ ID NO 114
<211> LENGTH: 20
<212> TYPE: DNA
<213> ORGANISM: Artificial Sequence
<220> FEATURE:
<223> OTHER INFORMATION: Oligonucleotide

<400> SEQUENCE: 114
gtttgccttg acttgaggta                                              20

<210> SEQ ID NO 115
<211> LENGTH: 19
<212> TYPE: DNA
<213> ORGANISM: Artificial Sequence
<220> FEATURE:
<223> OTHER INFORMATION: Oligonucleotide

<400> SEQUENCE: 115
tccccagttg attggaaga                                               19

<210> SEQ ID NO 116
<211> LENGTH: 21
<212> TYPE: DNA
<213> ORGANISM: Artificial Sequence
<220> FEATURE:
<223> OTHER INFORMATION: Oligonucleotide

<400> SEQUENCE: 116
agtcaaacct tccttcttgg a                                            21

<210> SEQ ID NO 117
<211> LENGTH: 22
<212> TYPE: DNA
<213> ORGANISM: Artificial Sequence
<220> FEATURE:
<223> OTHER INFORMATION: Oligonucleotide

<400> SEQUENCE: 117

```
gcttcaccct gtggaacgaa tc                                             22

<210> SEQ ID NO 118
<211> LENGTH: 21
<212> TYPE: DNA
<213> ORGANISM: Artificial Sequence
<220> FEATURE:
<223> OTHER INFORMATION: Oligonucleotide

<400> SEQUENCE: 118
ggagatgccc gtgatgaacc a                                              21

<210> SEQ ID NO 119
<211> LENGTH: 21
<212> TYPE: DNA
<213> ORGANISM: Artificial Sequence
<220> FEATURE:
<223> OTHER INFORMATION: Oligonucleotide

<400> SEQUENCE: 119
acctggaatc agattacttt g                                              21

<210> SEQ ID NO 120
<211> LENGTH: 19
<212> TYPE: DNA
<213> ORGANISM: Artificial Sequence
<220> FEATURE:
<223> OTHER INFORMATION: Oligonucleotide

<400> SEQUENCE: 120
ccatacctct aggctggct                                                 19

<210> SEQ ID NO 121
<211> LENGTH: 22
<212> TYPE: DNA
<213> ORGANISM: Artificial Sequence
<220> FEATURE:
<223> OTHER INFORMATION: Oligonucleotide

<400> SEQUENCE: 121
ccttcagcca gacagaatgt gt                                             22

<210> SEQ ID NO 122
<211> LENGTH: 19
<212> TYPE: DNA
<213> ORGANISM: Artificial Sequence
<220> FEATURE:
<223> OTHER INFORMATION: Oligonucleotide

<400> SEQUENCE: 122
gcaaacaggg ccagtacca                                                 19

<210> SEQ ID NO 123
<211> LENGTH: 25
<212> TYPE: DNA
<213> ORGANISM: Artificial Sequence
<220> FEATURE:
<223> OTHER INFORMATION: Oligonucleotide

<400> SEQUENCE: 123
tgtggaggct atggaagaag atatg                                          25

<210> SEQ ID NO 124
<211> LENGTH: 20
<212> TYPE: DNA
<213> ORGANISM: Artificial Sequence
```

<220> FEATURE:
<223> OTHER INFORMATION: Oligonucleotide

<400> SEQUENCE: 124
gtgcacccac ccatttcttg        20

<210> SEQ ID NO 125
<211> LENGTH: 24
<212> TYPE: DNA
<213> ORGANISM: Artificial Sequence
<220> FEATURE:
<223> OTHER INFORMATION: Oligonucleotide

<400> SEQUENCE: 125
acaacacaga cgttcgtctc attg        24

<210> SEQ ID NO 126
<211> LENGTH: 23
<212> TYPE: DNA
<213> ORGANISM: Artificial Sequence
<220> FEATURE:
<223> OTHER INFORMATION: Oligonucleotide

<400> SEQUENCE: 126
gaacagcact tcttcaaggg tga        23

<210> SEQ ID NO 127
<211> LENGTH: 25
<212> TYPE: DNA
<213> ORGANISM: Artificial Sequence
<220> FEATURE:
<223> OTHER INFORMATION: Oligonucleotide

<400> SEQUENCE: 127
cctgagctac agatatgtca ccaag        25

<210> SEQ ID NO 128
<211> LENGTH: 20
<212> TYPE: DNA
<213> ORGANISM: Artificial Sequence
<220> FEATURE:
<223> OTHER INFORMATION: Oligonucleotide

<400> SEQUENCE: 128
ggctggaaag tcaggactcg        20

<210> SEQ ID NO 129
<211> LENGTH: 24
<212> TYPE: DNA
<213> ORGANISM: Artificial Sequence
<220> FEATURE:
<223> OTHER INFORMATION: Oligonucleotide

<400> SEQUENCE: 129
gccatacgcc acccatgtca caac        24

<210> SEQ ID NO 130
<211> LENGTH: 24
<212> TYPE: DNA
<213> ORGANISM: Artificial Sequence
<220> FEATURE:
<223> OTHER INFORMATION: Oligonucleotide

<400> SEQUENCE: 130
gttggggcca catagcttgt ccag        24

<210> SEQ ID NO 131
<211> LENGTH: 29
<212> TYPE: DNA
<213> ORGANISM: Artificial Sequence
<220> FEATURE:
<223> OTHER INFORMATION: Oligonucleotide

<400> SEQUENCE: 131
gtggcagtgg ctgtcattgt tggagtggt                                29

<210> SEQ ID NO 132
<211> LENGTH: 29
<212> TYPE: DNA
<213> ORGANISM: Artificial Sequence
<220> FEATURE:
<223> OTHER INFORMATION: Oligonucleotide

<400> SEQUENCE: 132
tcatctgcgg ctgggtttgg tatttcttc                                29

<210> SEQ ID NO 133
<211> LENGTH: 23
<212> TYPE: DNA
<213> ORGANISM: Artificial Sequence
<220> FEATURE:
<223> OTHER INFORMATION: Oligonucleotide

<400> SEQUENCE: 133
ttgggagtgg acacctgcag tct                                      23

<210> SEQ ID NO 134
<211> LENGTH: 24
<212> TYPE: DNA
<213> ORGANISM: Artificial Sequence
<220> FEATURE:
<223> OTHER INFORMATION: Oligonucleotide

<400> SEQUENCE: 134
ccttggtgaa gcagctcttc agcc                                     24

<210> SEQ ID NO 135
<211> LENGTH: 22
<212> TYPE: DNA
<213> ORGANISM: Artificial Sequence
<220> FEATURE:
<223> OTHER INFORMATION: Oligonucleotide

<400> SEQUENCE: 135
gctcgtgata acggctaagg aa                                       22

<210> SEQ ID NO 136
<211> LENGTH: 20
<212> TYPE: DNA
<213> ORGANISM: Artificial Sequence
<220> FEATURE:
<223> OTHER INFORMATION: Oligonucleotide

<400> SEQUENCE: 136
cgatggaaga aaggcatcga                                          20

<210> SEQ ID NO 137
<211> LENGTH: 26
<212> TYPE: DNA
<213> ORGANISM: Artificial Sequence
<220> FEATURE:
<223> OTHER INFORMATION: Oligonucleotide

```
<400> SEQUENCE: 137
atggacgtga tggatggctg ccagtt                                          26

<210> SEQ ID NO 138
<211> LENGTH: 24
<212> TYPE: DNA
<213> ORGANISM: Artificial Sequence
<220> FEATURE:
<223> OTHER INFORMATION: Oligonucleotide

<400> SEQUENCE: 138
gcggcacaaa ctcgtcccca aatt                                            24

<210> SEQ ID NO 139
<211> LENGTH: 18
<212> TYPE: DNA
<213> ORGANISM: Artificial Sequence
<220> FEATURE:
<223> OTHER INFORMATION: Oligonucleotide

<400> SEQUENCE: 139
agcactacag cggcgact                                                   18

<210> SEQ ID NO 140
<211> LENGTH: 19
<212> TYPE: DNA
<213> ORGANISM: Artificial Sequence
<220> FEATURE:
<223> OTHER INFORMATION: Oligonucleotide

<400> SEQUENCE: 140
gcgactcaga aggcacgtc                                                  19

<210> SEQ ID NO 141
<211> LENGTH: 20
<212> TYPE: DNA
<213> ORGANISM: Artificial Sequence
<220> FEATURE:
<223> OTHER INFORMATION: Oligonucleotide

<400> SEQUENCE: 141
gacatccccc tacttctacc                                                 20

<210> SEQ ID NO 142
<211> LENGTH: 18
<212> TYPE: DNA
<213> ORGANISM: Artificial Sequence
<220> FEATURE:
<223> OTHER INFORMATION: Oligonucleotide

<400> SEQUENCE: 142
tcacgctcct cctggttg                                                   18

<210> SEQ ID NO 143
<211> LENGTH: 20
<212> TYPE: DNA
<213> ORGANISM: Artificial Sequence
<220> FEATURE:
<223> OTHER INFORMATION: Oligonucleotide

<400> SEQUENCE: 143
tgtgaatgcc aaatgtgctt                                                 20

<210> SEQ ID NO 144
```

```
<211> LENGTH: 20
<212> TYPE: DNA
<213> ORGANISM: Artificial Sequence
<220> FEATURE:
<223> OTHER INFORMATION: Oligonucleotide

<400> SEQUENCE: 144
gtggagctgg gtatccttga                                              20

<210> SEQ ID NO 145
<211> LENGTH: 20
<212> TYPE: DNA
<213> ORGANISM: Artificial Sequence
<220> FEATURE:
<223> OTHER INFORMATION: Oligonucleotide

<400> SEQUENCE: 145
ggaaacaatc attaccatgc                                              20

<210> SEQ ID NO 146
<211> LENGTH: 20
<212> TYPE: DNA
<213> ORGANISM: Artificial Sequence
<220> FEATURE:
<223> OTHER INFORMATION: Oligonucleotide

<400> SEQUENCE: 146
atccatagtt gggcctttac                                              20

<210> SEQ ID NO 147
<211> LENGTH: 20
<212> TYPE: DNA
<213> ORGANISM: Artificial Sequence
<220> FEATURE:
<223> OTHER INFORMATION: Oligonucleotide

<400> SEQUENCE: 147
agctttctat cctggccaca                                              20

<210> SEQ ID NO 148
<211> LENGTH: 21
<212> TYPE: DNA
<213> ORGANISM: Artificial Sequence
<220> FEATURE:
<223> OTHER INFORMATION: Oligonucleotide

<400> SEQUENCE: 148
gatcctgagt gtctgcagct t                                            21

<210> SEQ ID NO 149
<211> LENGTH: 20
<212> TYPE: DNA
<213> ORGANISM: Artificial Sequence
<220> FEATURE:
<223> OTHER INFORMATION: Oligonucleotide

<400> SEQUENCE: 149
ccagagggag aaaaactcca                                              20

<210> SEQ ID NO 150
<211> LENGTH: 20
<212> TYPE: DNA
<213> ORGANISM: Artificial Sequence
<220> FEATURE:
<223> OTHER INFORMATION: Oligonucleotide

<400> SEQUENCE: 150
```

```
ctgcacagac tctccacgag                                               20

<210> SEQ ID NO 151
<211> LENGTH: 20
<212> TYPE: DNA
<213> ORGANISM: Artificial Sequence
<220> FEATURE:
<223> OTHER INFORMATION: Oligonucleotide

<400> SEQUENCE: 151
caagattctt tgccgctacc                                               20

<210> SEQ ID NO 152
<211> LENGTH: 20
<212> TYPE: DNA
<213> ORGANISM: Artificial Sequence
<220> FEATURE:
<223> OTHER INFORMATION: Oligonucleotide

<400> SEQUENCE: 152
ttcagtggga ggtcaggttc                                               20

<210> SEQ ID NO 153
<211> LENGTH: 23
<212> TYPE: DNA
<213> ORGANISM: Artificial Sequence
<220> FEATURE:
<223> OTHER INFORMATION: Oligonucleotide

<400> SEQUENCE: 153
cccctgccca ttcggaggaa gag                                           23

<210> SEQ ID NO 154
<211> LENGTH: 23
<212> TYPE: DNA
<213> ORGANISM: Artificial Sequence
<220> FEATURE:
<223> OTHER INFORMATION: Oligonucleotide

<400> SEQUENCE: 154
ttggccacct tgacgctgcg gtg                                           23

<210> SEQ ID NO 155
<211> LENGTH: 20
<212> TYPE: DNA
<213> ORGANISM: Artificial Sequence
<220> FEATURE:
<223> OTHER INFORMATION: Oligonucleotide

<400> SEQUENCE: 155
gatccgctcc tttgatgatc                                               20

<210> SEQ ID NO 156
<211> LENGTH: 20
<212> TYPE: DNA
<213> ORGANISM: Artificial Sequence
<220> FEATURE:
<223> OTHER INFORMATION: Oligonucleotide

<400> SEQUENCE: 156
gtctcacact tgcatgccag                                               20

<210> SEQ ID NO 157
<211> LENGTH: 20
<212> TYPE: DNA
```

```
<213> ORGANISM: Artificial Sequence
<220> FEATURE:
<223> OTHER INFORMATION: Oligonucleotide

<400> SEQUENCE: 157
atcaatcagc ccagatggac                                                 20

<210> SEQ ID NO 158
<211> LENGTH: 20
<212> TYPE: DNA
<213> ORGANISM: Artificial Sequence
<220> FEATURE:
<223> OTHER INFORMATION: Oligonucleotide

<400> SEQUENCE: 158
ttcacgggca gaaaggtact                                                 20

<210> SEQ ID NO 159
<211> LENGTH: 20
<212> TYPE: DNA
<213> ORGANISM: Artificial Sequence
<220> FEATURE:
<223> OTHER INFORMATION: Oligonucleotide

<400> SEQUENCE: 159
aatgtctcca gcaccttcgt                                                 20

<210> SEQ ID NO 160
<211> LENGTH: 20
<212> TYPE: DNA
<213> ORGANISM: Artificial Sequence
<220> FEATURE:
<223> OTHER INFORMATION: Oligonucleotide

<400> SEQUENCE: 160
agcggatgtg gtaaggcata                                                 20

<210> SEQ ID NO 161
<211> LENGTH: 20
<212> TYPE: DNA
<213> ORGANISM: Artificial Sequence
<220> FEATURE:
<223> OTHER INFORMATION: Oligonucleotide

<400> SEQUENCE: 161
ctggcttcgt gcttacttcc                                                 20

<210> SEQ ID NO 162
<211> LENGTH: 20
<212> TYPE: DNA
<213> ORGANISM: Artificial Sequence
<220> FEATURE:
<223> OTHER INFORMATION: Oligonucleotide

<400> SEQUENCE: 162
cgggtgtgag gatgttctct                                                 20

<210> SEQ ID NO 163
<211> LENGTH: 21
<212> TYPE: DNA
<213> ORGANISM: Artificial Sequence
<220> FEATURE:
<223> OTHER INFORMATION: Oligonucleotide

<400> SEQUENCE: 163
ctcctattta atcctctcgt c                                               21
```

<210> SEQ ID NO 164
<211> LENGTH: 21
<212> TYPE: DNA
<213> ORGANISM: Artificial Sequence
<220> FEATURE:
<223> OTHER INFORMATION: Oligonucleotide

<400> SEQUENCE: 164
tactaccatc tcgcttatcc a                                              21

<210> SEQ ID NO 165
<211> LENGTH: 21
<212> TYPE: DNA
<213> ORGANISM: Artificial Sequence
<220> FEATURE:
<223> OTHER INFORMATION: Oligonucleotide

<400> SEQUENCE: 165
tgattggctc agttccacca g                                              21

<210> SEQ ID NO 166
<211> LENGTH: 20
<212> TYPE: DNA
<213> ORGANISM: Artificial Sequence
<220> FEATURE:
<223> OTHER INFORMATION: Oligonucleotide

<400> SEQUENCE: 166
aggttgctca gcacacactc                                                20

<210> SEQ ID NO 167
<211> LENGTH: 19
<212> TYPE: DNA
<213> ORGANISM: Artificial Sequence
<220> FEATURE:
<223> OTHER INFORMATION: Oligonucleotide

<400> SEQUENCE: 167
cggagcgagg aagggaaag                                                 19

<210> SEQ ID NO 168
<211> LENGTH: 23
<212> TYPE: DNA
<213> ORGANISM: Artificial Sequence
<220> FEATURE:
<223> OTHER INFORMATION: Oligonucleotide

<400> SEQUENCE: 168
ttggggataa actgcttgta ggc                                            23

<210> SEQ ID NO 169
<211> LENGTH: 20
<212> TYPE: DNA
<213> ORGANISM: Artificial Sequence
<220> FEATURE:
<223> OTHER INFORMATION: Oligonucleotide

<400> SEQUENCE: 169
accaactatt gcttcagctc                                                20

<210> SEQ ID NO 170
<211> LENGTH: 18
<212> TYPE: DNA
<213> ORGANISM: Artificial Sequence
<220> FEATURE:

<223> OTHER INFORMATION: Oligonucleotide

<400> SEQUENCE: 170
ttatgctggt tgtacagg                                                      18

<210> SEQ ID NO 171
<211> LENGTH: 19
<212> TYPE: DNA
<213> ORGANISM: Artificial Sequence
<220> FEATURE:
<223> OTHER INFORMATION: Oligonucleotide

<400> SEQUENCE: 171
tcgtctgcat ctcactcat                                                     19

<210> SEQ ID NO 172
<211> LENGTH: 19
<212> TYPE: DNA
<213> ORGANISM: Artificial Sequence
<220> FEATURE:
<223> OTHER INFORMATION: Oligonucleotide

<400> SEQUENCE: 172
gataaatctc tgcctcacg                                                     19

<210> SEQ ID NO 173
<211> LENGTH: 21
<212> TYPE: DNA
<213> ORGANISM: Artificial Sequence
<220> FEATURE:
<223> OTHER INFORMATION: Oligonucleotide

<400> SEQUENCE: 173
ctgtccctgc tgcacttttg t                                                  21

<210> SEQ ID NO 174
<211> LENGTH: 21
<212> TYPE: DNA
<213> ORGANISM: Artificial Sequence
<220> FEATURE:
<223> OTHER INFORMATION: Oligonucleotide

<400> SEQUENCE: 174
tcttccgccg gttggtctgt t                                                  21

<210> SEQ ID NO 175
<211> LENGTH: 20
<212> TYPE: DNA
<213> ORGANISM: Artificial Sequence
<220> FEATURE:
<223> OTHER INFORMATION: Oligonucleotide

<400> SEQUENCE: 175
cctttcagcc caatggagat                                                    20

<210> SEQ ID NO 176
<211> LENGTH: 20
<212> TYPE: DNA
<213> ORGANISM: Artificial Sequence
<220> FEATURE:
<223> OTHER INFORMATION: Oligonucleotide

<400> SEQUENCE: 176
acacagcagt tctcctccaa                                                    20

<210> SEQ ID NO 177
<211> LENGTH: 19
<212> TYPE: DNA
<213> ORGANISM: Artificial Sequence
<220> FEATURE:
<223> OTHER INFORMATION: Oligonucleotide

<400> SEQUENCE: 177
gcgggagcac ccctgtgtc                                                19

<210> SEQ ID NO 178
<211> LENGTH: 21
<212> TYPE: DNA
<213> ORGANISM: Artificial Sequence
<220> FEATURE:
<223> OTHER INFORMATION: Oligonucleotide

<400> SEQUENCE: 178
cccgagagcc tgtccagatg c                                             21

<210> SEQ ID NO 179
<211> LENGTH: 19
<212> TYPE: DNA
<213> ORGANISM: Artificial Sequence
<220> FEATURE:
<223> OTHER INFORMATION: Oligonucleotide

<400> SEQUENCE: 179
aatctgggcc atgatgcag                                                19

<210> SEQ ID NO 180
<211> LENGTH: 18
<212> TYPE: DNA
<213> ORGANISM: Artificial Sequence
<220> FEATURE:
<223> OTHER INFORMATION: Oligonucleotide

<400> SEQUENCE: 180
actgctgttt tccgaggc                                                 18

<210> SEQ ID NO 181
<211> LENGTH: 20
<212> TYPE: DNA
<213> ORGANISM: Artificial Sequence
<220> FEATURE:
<223> OTHER INFORMATION: Oligonucleotide

<400> SEQUENCE: 181
tcagcctctt ctccttcctg                                               20

<210> SEQ ID NO 182
<211> LENGTH: 20
<212> TYPE: DNA
<213> ORGANISM: Artificial Sequence
<220> FEATURE:
<223> OTHER INFORMATION: Oligonucleotide

<400> SEQUENCE: 182
tgaagaggac ctgggagtag                                               20

```
<210> SEQ ID NO 183
<211> LENGTH: 20
<212> TYPE: DNA
<213> ORGANISM: Artificial Sequence
<220> FEATURE:
<223> OTHER INFORMATION: Oligonucleotide

<400> SEQUENCE: 183
accaagtgcc acaaaggaac                                               20

<210> SEQ ID NO 184
<211> LENGTH: 20
<212> TYPE: DNA
<213> ORGANISM: Artificial Sequence
<220> FEATURE:
<223> OTHER INFORMATION: Oligonucleotide

<400> SEQUENCE: 184
ctgcaattga agcactggaa                                               20

<210> SEQ ID NO 185
<211> LENGTH: 20
<212> TYPE: DNA
<213> ORGANISM: Artificial Sequence
<220> FEATURE:
<223> OTHER INFORMATION: Oligonucleotide

<400> SEQUENCE: 185
ttcgctcttc cagttggact                                               20

<210> SEQ ID NO 186
<211> LENGTH: 20
<212> TYPE: DNA
<213> ORGANISM: Artificial Sequence
<220> FEATURE:
<223> OTHER INFORMATION: Oligonucleotide

<400> SEQUENCE: 186
caccagggga agaatctgag                                               20

<210> SEQ ID NO 187
<211> LENGTH: 21
<212> TYPE: DNA
<213> ORGANISM: Artificial Sequence
<220> FEATURE:
<223> OTHER INFORMATION: Oligonucleotide

<400> SEQUENCE: 187
caatgtcacc agtgacctca a                                             21

<210> SEQ ID NO 188
<211> LENGTH: 20
<212> TYPE: DNA
<213> ORGANISM: Artificial Sequence
<220> FEATURE:
<223> OTHER INFORMATION: Oligonucleotide

<400> SEQUENCE: 188
tgaactcgaa agggttgtcc                                               20
```